(12) United States Patent
Gao et al.

(10) Patent No.: US 9,133,245 B2
(45) Date of Patent: Sep. 15, 2015

(54) CYCLIC LACTADHERIN PEPTIDE MIMETICS AND THEIR USES

(75) Inventors: Jianmin Gao, Newton, MA (US); Hong Zheng, Brighton, MA (US)

(73) Assignee: TRUSTEES OF BOSTON COLLEGE, Chestnut Hill, MA (US)

( * ) Notice: Subject to any disclaimer, the term of this patent is extended or adjusted under 35 U.S.C. 154(b) by 0 days.

(21) Appl. No.: 14/125,906

(22) PCT Filed: May 24, 2012

(86) PCT No.: PCT/US2012/039255
§ 371 (c)(1),
(2), (4) Date: Mar. 10, 2014

(87) PCT Pub. No.: WO2012/173762
PCT Pub. Date: Dec. 20, 2012

(65) Prior Publication Data
US 2014/0194369 A1    Jul. 10, 2014

Related U.S. Application Data

(60) Provisional application No. 61/496,324, filed on Jun. 13, 2011, provisional application No. 61/500,883, filed on Jun. 24, 2011.

(51) Int. Cl.
| | | |
|---|---|---|
| C07K 7/64 | (2006.01) |
| A61K 49/00 | (2006.01) |
| A61K 49/08 | (2006.01) |
| A61K 49/14 | (2006.01) |
| A61K 51/08 | (2006.01) |
| G01N 33/92 | (2006.01) |
| A61K 38/00 | (2006.01) |

(52) U.S. Cl.
CPC .............. *C07K 7/64* (2013.01); *A61K 49/0043* (2013.01); *A61K 49/0056* (2013.01); *A61K 49/085* (2013.01); *A61K 49/14* (2013.01); *A61K 51/088* (2013.01); *G01N 33/92* (2013.01); *A61K 38/00* (2013.01); *G01N 2510/00* (2013.01)

(58) Field of Classification Search
CPC ....... A61K 38/12; A61K 38/08; A61K 38/10; A61K 38/13; C07K 7/06; C07K 7/64; C07K 7/08; C07K 7/645; C07K 7/52; C07K 7/60; C12P 21/00
See application file for complete search history.

(56) References Cited

U.S. PATENT DOCUMENTS

| | | |
|---|---|---|
| 7,771,956 B2 | 8/2010 | Gilbert et al. |
| 2004/0241179 A1 | 12/2004 | Raposo et al. |
| 2007/0249526 A1 | 10/2007 | Abbenante et al. |
| 2010/0074920 A1 | 3/2010 | Natunen et al. |

OTHER PUBLICATIONS

O'Leary et. al.; Structure-Activity Relationships of Conformationally Constrained Peptide analogues of Loop 2 of Brain-Derived Neurotrophic Factor, J. of Neurochem., vol. 70:1712-1721 (1998).*

(Continued)

*Primary Examiner* — James H Alstrum Acevedo
*Assistant Examiner* — Randall L Beane
(74) *Attorney, Agent, or Firm* — Nixon Peabody LLP; Ronald I. Eisenstein

(57) ABSTRACT

Provided herein is a new class of cyclic lactadherin peptides (cLac) that mimic the natural phosphatidylserine (PS)-binding activity of the parent lactadherin protein. These cLacs are useful as small molecule indicators of early stage of apoptosis and of treatment efficacy evaluation.

19 Claims, 18 Drawing Sheets cLac-Bip

(56) References Cited

OTHER PUBLICATIONS

Zhang et al.; Lactone and Lactam Library Synthesis by Silver Ion-Assisted Orthogonal Cyclization of Unprotected Peptides, J. Am. Chem. Soc., vol. 121:3311-3320 (1999).*

Paborsky et al.; A peptide Derived from a Tissue Factor Loop Region Functions as a Tissue Factor-Factor VIIa Antagonist, Biochemistry, vol. 34:15328-15333 (1995).*

Livingstone et al. (Cabios, vol. 9(6):745-756 (1993).*

Edington L.E. et al. Nat Med. 15(8):967-973 (Aug. 2009). doi: 10.1038/nm.1938. Epub Jul. 13, 2009."Noninvasive optical imaging of apoptosis by caspase-targeted activity-based probes."

Fens, M.H.A.M. et al., Blood. 111:4542-4550 (Feb. 21, 2008) Abstract. "Angiogenic endothelium shows lactadherin-dependent phagocytosis of aged erythrocytes and apoptotic cells."

Park D. et al., J Am Chem Soc. 133(9):2832-2835 (Mar. 9, 2011). doi: 10.1021/ja110226y. Epub Feb. 15, 2011. Noninvasive imaging of cell death using an Hsp90 ligand.

Shao, C. et al., JBC 283(11):7230-7241 (Mar. 14, 2008). Abstract. "Crystal Structure of Lactadherin C2 Domain at 1.7A Resolution with Mutational and Computational Analyses of Its Membrane-binding Motif."

Smith B.A. et al., Apoptosis.16(7):722-731 (Jul. 2011). doi: 10.1007/s10495-011-0601-5. "In vivo targeting of cell death using a synthetic fluorescent molecular probe."

Thapa N. et al., J Cell Mol Med. 12(5A):1649-1660 (Sep.-Oct. 2008). doi: 10.1111/j.1582-4934.2008.00305.x. Epub Mar. 14, 2008. "Discovery of a phosphatidylserine-recognizing peptide and its utility in molecular imaging of tumour apoptosis."

Zheng, H. et al., J. Am. Chem. Soc. 133(39):15280-15283 (Sep. 7, 2011). "Cofactor-Free Detection of Phosphatidylserine with Cyclic Peptides Mimicking Lactadherin."

* cited by examiner

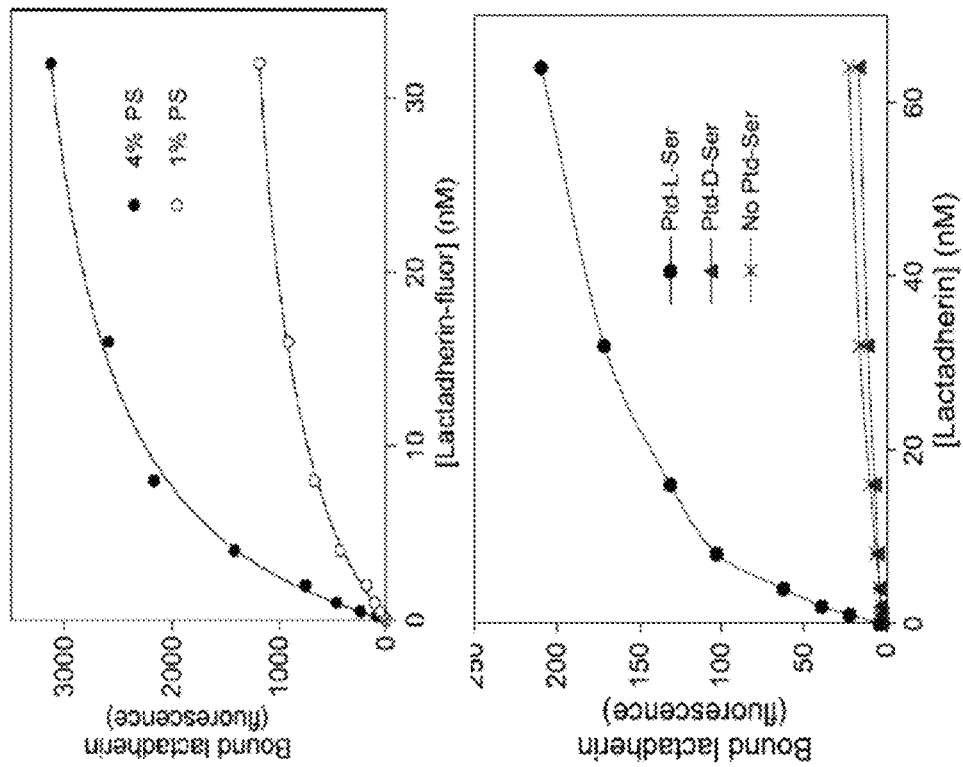
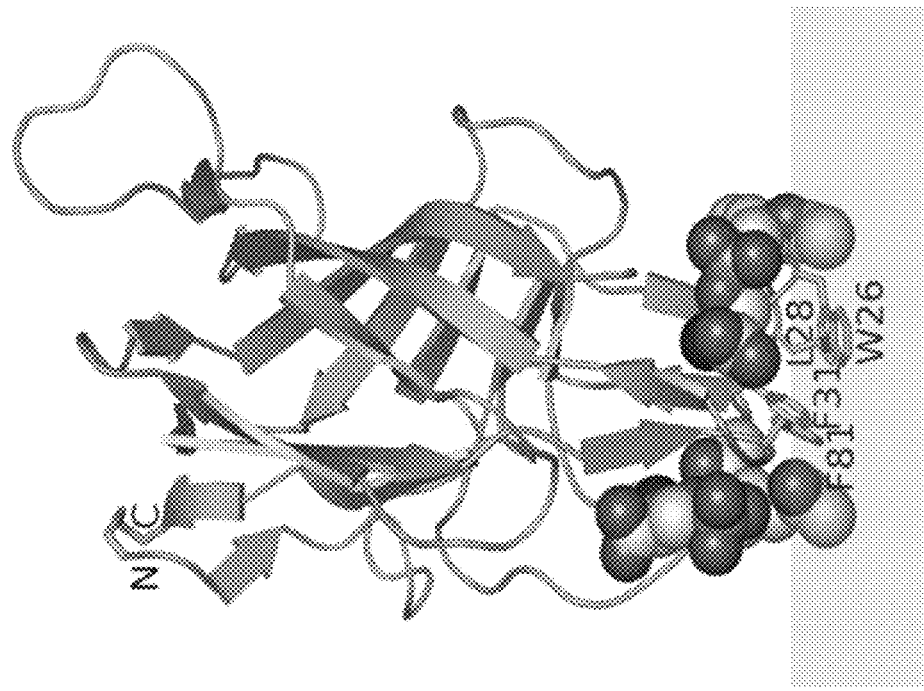
*FIGURE 3A*
*FIGURE 3B*

SEQUENCE LISTING

```
<160> NUMBER OF SEQ ID NOS: 45

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 1

Trp Phe Gly His Ile Gln Gly Gly Arg Gly Gly Gly Asp
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 2

Trp Phe Gly His Ile Gln Ala Gly Arg Gly Gly Gly Asp
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 3

Trp Phe Gly His Ile Gln Gly Ala Arg Gly Gly Gly Asp
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 4

Trp Phe Gly His Ile Gln Gly Gly Arg Gly Gly Ala Asp
1               5                   10

<210> SEQ ID NO 5
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 5

Trp Phe Gly His Ile Gln Gly Gly Arg Gly Gly Gly Asp
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 6

Trp Phe Gly His Ile Gln Gly Gly Arg Gly Gly Gly Gly Gly Asp
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine
<220> FEATURE:
<221> NAME/KEY: MOD_RES
<222> LOCATION: (5)..(5)
<223> OTHER INFORMATION: Propargyl glycine

<400> SEQUENCE: 7

Trp Phe Gly His Gly Gln Gly Gly Arg Gly Gly Gly Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine
<220> FEATURE:
<221> NAME/KEY: MOD_RES
<222> LOCATION: (8)..(8)
<223> OTHER INFORMATION: Propargyl glycine

<400> SEQUENCE: 8

Trp Phe Gly His Ile Gln Gly Gly Arg Gly Gly Gly Asp
1               5                   10

<210> SEQ ID NO 9
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 9

Trp Phe Gly His Ile Gln Gly Arg Gly Gly Gly Asp
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 10

Trp Phe Gly His Ile Gln Gly Gly Gly Arg Gly Gly Gly Asp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine
<220> FEATURE:
<221> NAME/KEY: MOD_RES
<222> LOCATION: (8)..(8)
<223> OTHER INFORMATION: Propargyl glycine

<400> SEQUENCE: 11

Trp Phe Gly His Ile Gln Gly Gly Arg Gly Gly Ala Asp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: Biphenylalanine

<400> SEQUENCE: 12

Trp Phe Gly His Ile Gln Gly Gly Arg Gly Gly Gly Asp
1               5                   10

<210> SEQ ID NO 13
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala Ala
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Ile Ile Ile Ile
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Val Val Val Val
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Val Ala Val
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ile Gly Val
```

```
<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Ala Val Ala
1

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ile Ile Ile Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Gly Val Ala Val
1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Val Val Val
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Ile Ile Ile
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 24

Leu Leu Leu Leu
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Cys Cys Cys
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ser Ser Ser
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Thr Thr Thr
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Trp Trp Trp
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Tyr Tyr Tyr
1

<210> SEQ ID NO 30

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Pro Pro Pro
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Phe Phe Phe
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Met Met Met
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Gln Gln
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Asn Asn Asn
1

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Trp Gly His Ile Gln Gly Arg Gly Gly Gly Asp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gly Arg Gly Gln Ile His Gly Trp Asp
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Gly His Ile Gln Gly Gly Arg Gly Gly Gly Asp
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Phe Gly His Ile Gln Gly Gly Arg Gly Gly Gly Asp
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Terphenylalanine

<400> SEQUENCE: 39

Trp Phe Gly His Ile Gln Gly Gly Arg Gly Gly Gly Asp
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 40

Trp Phe Gly His Ile Gln Gly Gly Arg Ala Gly Gly Asp
```

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 41

Trp Phe Gly His Ile Gln Gly Gly Arg Gly Ala Gly Asp
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Biphenylalanine

<400> SEQUENCE: 42

Trp Phe Gly His Ile Gln Gly Gly Arg Gly Gly Asp
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: Biphenylalanine

<400> SEQUENCE: 43

Trp Phe Gly His Ile Gln Gly Gly Arg Gly Gly Gly
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: Biphenylalanine

<400> SEQUENCE: 44

```
Trp Phe Gly His Ile Gln Gly Gly Arg Gly Gly Gly Gly
1               5                   10
```

```
<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1 to 8 "Gly Gly Gly
      Gly Ser" repeating units
<220> FEATURE:
<223> OTHER INFORMATION: see specification as filed for detailed
      description of substitutions and preferred embodiments

<400> SEQUENCE: 45

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser Gly Gly Gly Gly Ser
            35                  40
```

CYCLIC LACTADHERIN PEPTIDE MIMETICS AND THEIR USES

CROSS REFERENCE TO RELATED APPLICATIONS

This application is a 35 U.S.C. §371 National Phase Entry Application of International Application No. PCT/US2012/039255 filed May 24, 2012, which designates the U.S., and which claims benefit under 35 U.S.C. §119(e) of U.S. Provisional Application No. 61/496,324 filed Jun. 13, 2011 and U.S. Provisional Application No. 61/500,883 filed Jun. 24, 2011, the contents of each of which are incorporated herein by reference in their entireties.

SEQUENCE LISTING

The instant application contains a sequence listing which has been submitted in ASCII format via EFS-Web and is hereby incorporated by reference in its entirety. The ASCII copy, created on Nov. 14, 2013, is named 051566-071003-US_SL.txt and is 12,385 bytes in size.

FIELD

Embodiments described herein generally relate to indicator molecules for phosphatidylserine (PS)-containing lipid membranes and detection of apoptosis.

BACKGROUND

The lipid composition and distribution of cell membranes play an important role in regulating the physiology of the cell. For example, numerous signaling proteins can be recruited to the membrane by clusters of negatively charged lipids. Live mammalian cells actively maintain an asymmetric lipid distribution on their plasma membrane (see FIG. 1B), with phosphatidylserine (PS), the most abundant anionic lipid, completely confined to the cytosolic leaflet. PS externalization has been observed for cells under abnormal development, including apoptotic cells, activated platelets, and virus-infected cells. In fact, imaging PS exposure has been a benchmark approach to detect apoptotic cells in research laboratories.

Among the limited number of PS-targeting ligands, annexin V is best established for detecting apoptotic cells in vitro and in living organisms. This naturally occurring 36 kDa protein have been labeled with fluoro-chromes or radioactive nuclides and used to studies such as imaging cell death in animal models of human cancer, as well as in humans. However, there are some drawbacks with using annexin V. Annexin V is less ideal as an indicator molecule for the presence of PS because of its large size, high cost, and calcium dependence for PS recognition (see FIG. 2). In addition, the moderate stability and slow clearance severely limit its application in vivo. Small molecules that specifically target PS may circumvent the problems afflicting annexin V and their development has captured increasing attention. There is a class of bivalent organozinc complexes that functionally mimic annexin V and selectively associate with negatively charged membranes. Recently, screening of phage-displayed peptide libraries has also yielded promising lead sequences for PS recognition.

SUMMARY

It is the objective of this disclosure to provide alternative indicator molecules for the detection of phosphatidylserine (PS) that circumvent the drawbacks present in annexin V, such as bulky size, co-factor dependent, and low clearance.

Provided herein are small molecule receptors or indicator molecules for detecting/recognition of PS. The indicator molecules are cyclic lactadherin peptide mimetics (cLacs) designed to mimic the natural phosphatidylserine (PS)-binding protein lactadherin (Lac). Taking a biomimetic approach, the inventors grafted the key residues of Lac into a cyclic peptide scaffold. Importantly, and in contrast to the parent protein Lac, the cLacs do not require cofactors for PS recognition. These cLac are generally less than 20 amino acids. The fluorophore-labeled cLac selectively stains apoptotic cells by targeting PS on cell surfaces.

These cyclic lactadherin mimics (cLacs) selectively associate with PS-presenting membranes with low micromolar affinity. The inventors further demonstrate that a fluorescently labeled cLac readily stains cells at the early stage of apoptosis. Importantly, the cLac-PS recognition described herein does not require any metal cofactors, which is in contrast and distinct from annexin V and its small molecule mimetics, and from other organozinc complexes. The small size, ease of labeling, and cofactor-free PS recognition make the cLac peptides highly useful for imaging apoptosis in cell cultures as well as in living organisms. Given that many cancer therapeutics are designed to elicit apoptosis of cancer cells, non-invasive imaging of PS using the cLacs can enable facile evaluation of the efficacy of anti-cancer drugs.

Accordingly, provided herein are cLacs peptide mimetics that bind PS and uses thereof.

In one embodiment, provided herein is a cyclic peptide (cLac) comprising at least 10 but no more than 20 amino acid residues having the formula I:

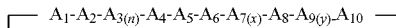

$$A_1\text{-}A_2\text{-}A_{3(n)}\text{-}A_4\text{-}A_5\text{-}A_6\text{-}A_{7(x)}\text{-}A_8\text{-}A_{9(y)}\text{-}A_{10}$$

wherein $A^1$ and $A^2$ are hydrophobic amino acid residues that are appropriate for lipid membrane binding or membrane insertion, wherein the side chains of A1 and A2 have an added cLogP value of between 5 and 9, and wherein the hydrophobic amino acid residues are in the D or L configuration, are natural or unnatural amino acid residues, and hydrophobic amino acid are substituted or unsubstituted;

wherein $A_4$ is an amino acid with polar side chain that can form strong hydrogen bonding or salt bridge;

wherein $A_5$ is a small hydrophobic amino acid;

wherein $A_6$ is an amino acid with polar side chain that can form strong hydrogen bonding;

wherein $A_3$, $A_7$ and $A_9$ are neutral amino acid residues, wherein n=1-3, x=1-5 and y=2-6, and when there are multiples of $A_3$, $A_7$ and $A_9$, they can be the same amino acid residues or different amino acid residues;

wherein $A_8$ is a positively charged amino acid and can be present or absent; and wherein $A_{10}$ is an amino acid with a negatively charged side chain.

In some embodiments of the cLacs described herein, the substituent or substituted hydrophobic amino acid is a halogenated aromatic or aliphatic amino acid, a halogenated aliphatic or aromatic modification on the hydrophobic side chain, or an aliphatic or aromatic modification.

In some embodiments of the cLacs described herein, the aliphatic modification is between 1 to 10 carbons, 1 to 6 carbons, or 1 to 4 carbons, and wherein the aliphatic modification is straight chain alkyl or alkenyl.

In some embodiments of the cLacs described herein, $A_1$ and $A_2$ are each individually selected from the group consisting of alanine, glycine, histidine, proline, serine, threonine, tyrosine, cysteine, methionine, valine, tryptophan, phenylalanine, leucine, isoleucine, biphenylalanine, methyl-phenylalanine, terphenylalnine, p-phenyl-L-phenylalanine, 3-(2-naphthyl)-L-alanine, 3-(1-naphthyl)-L-alanine, 4-Iodo-L-phenylalanine, 4-tert-bultyl-L-phenylalanine, 4-Bromo-L-phenylalanine, 3,4,5-Trifluoro-L-phenylalanine, and pentafluoro-L-phenylalanine.

In some embodiments of the cLacs described herein, $A_4$ is selected from the group consisting of histidine, asparagine, glutamine, lysine, arginine and its analogues and derivatives.

In some embodiments of the cLacs described herein, $A_5$ is selected from the group consisting of isoleucine, alanine, valine, leucine and methionine.

In some embodiments of the cLacs described herein, $A_6$ is selected from the group consisting of glutamine, tyrosine, serine, asparagine, histidine, cysteine and threonine.

In some embodiments of the cLacs described herein, $A_3$, $A_7$ and $A_9$ are each individually selected from the group consisting of glycine, alanine, valine, leucine, isoleucine, cysteine, tyrosine, tryptophan, serine, threonine, proline, methionine, phenylalanine, glutamine, asparagine and propargyl glycine (ppG).

In some embodiments of the cLacs described herein, $A_3$, $A_7$ and $A_9$ are each individually alanine or glycine.

In some embodiments of the cLacs described herein, $A_8$ is selected from the group consisting of lysine, arginine and the analogues and derivatives of these amino acids.

In some embodiments of the cLacs described herein, $A_{10}$ is selected from the group consisting of aspartic acid, glutamic acid and the analogues and derivatives of these amino acids.

In some embodiments of the cLacs described herein, the cLac binds to phosphatidylserine.

In some embodiments of the cLacs described herein, any of the amino acid can be in either the D- or L-configuration.

In some embodiments of the cLacs described herein, the cLac further comprises internal linkage(s) between the amino acids making up the circular scaffold of the cyclic peptide in addition to the standard peptide linkages. In some embodiments, the internal linkages are extra linkages that function to stabilize the cyclic peptide. In some embodiments, the internal linkages are known as "backside stapling" linkages. Accordingly, in some embodiments of the cLacs described herein, the cLacs further comprises a linker.

In one aspect, the cLac is a cyclic peptide comprising the sequence of WBipGHIQGGRGGGD (SEQ ID NO: 1) or a cyclic peptide variant thereof that selectively binds to PS. In another aspect, the cLac is a cyclic peptide consisting essentially of the sequence of WBipGHIQGGRGGGD (SEQ ID NO: 1) or a cyclic peptide variant thereof that selectively binds to PS. In some embodiments of this aspect, the cLac is selected from cLac-A1 or WBipGHIQAGRGGGD (SEQ ID NO: 2); cLac-A2 or WBipGHIQGARGGGD (SEQ ID NO: 3); cLac-A5 or WBipGHIQGGRGGAD (SEQ ID NO: 4); cLac-24G or WBipGHIQGGRGGGGD (SEQ ID NO: 5); cLac-25G or WBipGHIQGGRGGGGGD (SEQ ID NO: 6); cLac-PPG-0 or WBipGHppGQGGRGGGD (SEQ ID NO: 7); WBipGHIQGppGRGGGD (SEQ ID NO: 8), WBipGHIQGRGGGD (SEQ ID NO: 9), WBipGHIQGGGRGGGD (SEQ ID NO: 10), cLac-PPG-2 or WBipGHIQGppGRGGAD (SEQ ID NO: 11), D-WBipGHIQGGRGGGD (SEQ ID NO: 12) or a peptide variant thereof.

In some embodiments of the cLac described herein, the cLac is less than 30 amino acids. Accordingly, the cLac can be less than 25 amino acids, less than 20 amino acids, less than 19 amino acids, less than 18 amino acids, less than 17 amino acids, less than 16 amino acids, less than 15-amino acids, less than 14 amino acids, less than 13 amino acids, less than 12 amino acids, less than 11 amino acids, or less than 10 amino acids. In one embodiment, the cLac peptides described herein have 20 amino acids or less. In another embodiment, the cLac has more than 10 amino acids but no more than 20 amino acids. Accordingly, in some preferred embodiments, the cLac has 10, 11, 12, 13, 14, 15, 16, 17, 18, 19 or 20 amino acids.

In some embodiments of the cLacs described herein, the cLac further comprises a detectable label. In another embodiment, the cLac further comprises at least one detectable label.

In some embodiments of the cLacs described herein, wherein the label is a fluorescent label, a magnetic resonance imaging contrast label or positron emission tomography imaging label. In some embodiments of the cLacs described herein, the label is a radiolabel.

In one aspect, provided herein are methods of detecting PS exposure on a cell, comprising contacting a biological sample with a labeled cLac or peptide variant thereof or with a composition described herein, wherein detection of a change in a detectable signal produced by the label is indicative of PS exposure on a cell in the biological sample.

In another aspect, provided herein are methods of detecting apoptosis of a cell or a tissue, comprising contacting a biological sample with a labeled cLac or peptide variant thereof or a composition described herein, wherein detection of a change in a detectable signal produced by the label is indicative of apoptosis in the biological sample. Examples of tissue include but are not limited to muscle, breast, liver, and lung.

The results described herein indicate that cyclic lactahedrin mimics can be employed in a variety of clinical settings in which apoptotic and/or necrotic cell death need to be monitored in a subject, such as, without limitation, cancer therapy, organ and bone marrow transplant rejection or injury, infectious and non-infectious inflammatory diseases, autoimmune disease, cerebral and myocardial infarction and ischemia, cardiomyopathies, atherosclerative disease, neural and neuromuscular degenerative diseases, sickle cell disease, β-thalassemia, AIDS, myelodysplastic syndromes, and toxin-induced liver disease, etc. Cyclic lactahedrin mimics described herein can be labeled, for example, to image and quantify apoptotic cell death in normal and malignant tissues undergoing treatment. Monitoring apoptosis with serial imaging studies using cLacs can be used for the rapid testing and development of new drugs and therapies in a variety of diseases. In addition, the methods described herein can be used to monitor the progress of treatment, monitor the progress of disease, or both. Further, they can be used to aid in early detection of certain diseases.

Applications for the cLac and peptide variants thereof and the methods for detecting PS and apoptosis of cells described herein include detection of insufficient apoptosis when apoptosis should occur or is preferred, e.g., tumors or cells infected with virus, or detection of inappropriate or excess apoptosis in disease states when it should not occur, e.g., immune disorders such as lupus, transplant rejection, or in cells subject to severe ischemia.

Accordingly, in one aspect, provided herein are methods of detecting apoptosis in a subject in need thereof, comprising administering to a subject in need thereof an effective amount of a labeled cLac or labeled peptide variant or a composition described herein, wherein detection of a change in a detectable signal produced by the label is indicative of apoptosis in the subject in need thereof. Situations where apoptosis is known to occur include but are not limited to organ and bone marrow transplant rejection or injury, infectious and non-infectious inflammatory diseases, autoimmune disease, cerebral and myocardial infarction and ischemia, cardiomyopathies, atherosclerative disease, neural and neuromuscular degenerative diseases, sickle cell disease, β-thalassemia, AIDS, myelodysplastic syndromes, and toxin-induced liver disease. In some embodiments of the aspect, the subject in need thereof has cancer or a malignant condition. In some such embodiments, the subject having cancer or a malignant condition is receiving or undergoing a cancer therapy. In one embodiment, the method further comprises selecting a subject in need of detecting apoptosis and/or monitoring of apoptosis. Examples of such subjects are individuals being treated with a cytotoxic drug or therapy, e.g., for cancer; and individuals who have had an organ transplant.

In another aspect, provided herein are methods of determining efficacy of a treatment in a subject in need thereof, comprising (i) detecting a level of apoptosis in the subject using any of the methods described herein prior to administering a treatment and (ii) detecting a level of apoptosis in the subject using any of the methods described herein after administering the treatment, wherein a difference in the level of apoptosis in the subject after administering the treatment relative to the level of apoptosis in the subject before administering the treatment is indicative of the treatment being effective. In some embodiments of the method, the difference is an increase, e.g., in cancer treatment. In other embodiments of the method, the difference is a decrease, e.g., in organ transplant rejection, occlusion vascular disease, or infection.

In one embodiment, the treatment is a cancer therapy. In another embodiment, the treatment is organ transplant.

In one embodiment, provided herein is a composition comprising at least a cLac peptide described herein and a pharmaceutically acceptable carrier. The composition can have more than one cLac peptide described herein and the cLac peptides are different. In one embodiment of any of one of the compositions described herein, the at least one cLac peptide is labeled.

Also provided herein are kits for detecting PS exposure or apoptosis, comprising any of or at least one of the cLac or peptide derivatives thereof or a composition described herein and instructions for using the cLac to detect PS exposure or apoptosis in a cell or biological sample.

DEFINITIONS

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word or is intended to include and unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, a "cyclic lactahedrin mimic" or "cLac" that "selectively binds to" or is "specific for" phosphatidylserine (PS) refers to a cyclic lactahedrin peptide mimic as described herein that can selectively react with or bind to phosphatidylserine, but has little or no detectable reactivity to other lipid membrane that do not contained exposed PS that is accessible to the cLac, such as other phoshholipids, glycolipids, or cholesterols. For example, a cyclic lactahedrin mimic specific for PS will not identify or bind to phosphatidylcholines (PC), phosphatidylethanolamines (PE), or phosphatidylinositol (PI). In another embodiment, the cLac binds PS-containing membrane more than other PS-absent, lipid membrane, i.e., binds PS-containing membrane above the background binding or background signal to any PS-absent, lipid membrane, e.g., PC/cholesterol membrane or PC/PI membrane. In another embodiment, the increased binding of cLac to PS over that of the background binding in the absence of PS is at least 10%. Assay of cLac binding to lipid membranes can be measured by any method known in the art, for example, by liposome binding and fluorescence resonance energy transfer (FRET) described herein.

As used herein, in one embodiment, the terms "increased" or "increase" means an increase of at least 5% as compared to a control reference level of cLac binding in the absence of PS or healthy non-apoptotic cells. In other embodiment, the terms "increased" or "increase" means an increase of at least 5% as compared to a background signal of the label in the absence of labeled cLac. In some embodiments, an increase of at least 10%, at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to the background level of cLac binding in the absence of PS.

As used herein, "cyclic lactahedrin mimic", "cyclic lactahedrin peptide mimic", "cyclic lactahedrin mimetic", "cyclic lactahedrin peptide mimetic", "cyclic peptide", "cyclic lactahedrin peptide variant', "cyclic peptide variant", "cLac peptide variant" and "cLac variant" are used interchangeably and refers to a cyclic peptide of formula I that binds lipid membrane and specifically binds PS. In one embodiment, "cLac" encompasses variant forms of cLac.

As used herein, the term "peptide variants", "cLac peptide variant" or "peptide variant" refers to a peptide differing from cLac-2, the reference peptide, but substantially retaining the property of selectively binding to PS. By "substantially retaining selectively binding to PS" means that the "peptide variants" retain at least 10% of the selective binding to PS seen in the reference peptide cLac-2. The reference peptide cLac-2 is also known as Lac-Bip, cLac-Bip, and cLac-23G. In other embodiments, the "peptide variants" retain at least about 20%, at least about 30%, or at least about 40%, or at least about 50%, or at least about 60%, or at least about 70%, or at least about 80%, or at least about 90%, or at least about 100%, or at least about 120%, or at least about 140%, or at least about 160%, or at least about 180%, or at least about 200%, or at least about 250%, or at least about 300%, or at least about 350%, or at least about 400%, or up to and including a 1000% increase or any increase between 10-1000% as compared to the reference peptide cLac level, or at least about a 2-fold, or at least about a 3-fold, or at least about a 4-fold, or at least about a 5-fold, or at least about a 10-fold, or at least about a 20-fold, or at least about a 40-fold, or at least about a 60-fold, or at least about a 80-fold, or at least about a 100-fold increase, or any increase between 2-fold and 100-fold over the reference peptide cLac level. Generally, variants are overall closely similar, and, in many regions, identical to the reference peptide. As used herein, "cLac variant" refers to a cLac peptide of Formula I that differs from the amino acid sequences of amino acid of SEQ. ID. NOS: 1-12 or those identified in Table 2, but that retains lipid membrane binding and specific PS binding that are measured as described elsewhere herein or otherwise known in the art.

Accordingly, as used herein, "selectively binds" or "specifically binds" refers to the ability of a cLac described herein to bind to PS with a KDa of at least $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. Specific binding can be influenced by, for example, the affinity and avidity of the cyclic lactahedrin mimic or variant thereof and the concentration of the cyclic lactahedrin mimic or variant thereof.

As used herein, "label" or "detectable label" refers to any moiety or molecule that can be used to provide a detectable signal. A "labeled cLac" or "labeled cyclic lactadherin mimic," is one linked to a detectable label. The term "linked" encompasses covalently and non-covalently bonded, e.g., by hydrogen, ionic, or Van der Waals bonds. Such bonds can be formed between at least two of the same or different atoms or ions as a result of redistribution of electron densities of those atoms or ions. Labels can provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. Accordingly, the term "label", as used herein, refers to a moiety, molecule or composition capable of producing a detectable signal indicative of the presence of a target, such as, the presence of a specific cell-surface marker, such as phosphatidylserine, in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means for use with the cyclic lactadherin mimics described herein. A fluorescent dye is an embodiment of a label according to the methods described herein.

As used herein, the term "apoptosis" refers to the process of "programmed cell death" in a cell, whereby the cell executes a "cell suicide" program. The decision by a cell to undergo apoptosis can be influenced by a variety of regulatory stimuli and environmental factors. It has been recognized that membrane asymmetry, detected as appearance of PS (phosphatidyl serine) on the outer leaflet of the plasma membrane ("PS exposure"), is one of the earliest manifestations of apoptosis, preceding DNA fragmentation, plasma membrane blebbing, and loss of membrane integrity. Physiological activators of apoptosis include tumor necrosis factor (TNF), Fas ligand, transforming growth factor β, the neurotransmitters glutamate, dopamine, N-methyl-D-asparate, withdrawal of growth factors, loss of matrix attachment, calcium and glucocorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation (antimetabolites). Therapy-associated apoptosis inducers include gamma radiation, UV radiation and a variety of chemotherapeutic drugs, including cisplatin, doxorubicin, bleomycin, cytosine arabinoside, nitrogen mustard, methotrexate and vincristine. Toxin-related inducers or apoptosis include ethanol and d-amyloid peptide.

As used herein, "necrosis" refers to the localized death of cells or tissue due to causes other than apoptosis (i.e., other than the execution of the cell's intrinsic suicide program). Necrosis can be caused by traumatic injury, bacterial infection, acute hypoxia and the like. There is some overlap between the two types of cell death, in that some stimuli can cause either necrosis or apoptosis or some of both.

The term "biological sample" as used herein refers to a cell or population of cells or a quantity of tissue or fluid from a subject comprising one or more cells that may be undergoing apoptosis. Most often, the biological sample has been removed from a subject, but the term "biological sample" can also refer to cells or tissue analyzed in vivo, i.e., without removal from the subject, for example, in a subject having cancer. Biological samples include, but are not limited to, whole blood, bone marrow, tissue sample or biopsies, scrapes (e.g., buccal scrapes), plasma, umbilical cord blood, serum, urine, saliva, cell culture, cerebrospinal fluid, tumors, organs, and also samples obtained from in vitro cell cultures.

The terms "subject", "patient" and "individual" are used interchangeably herein, and refer to an animal. The term "subject" as used herein includes, without limitation, a human, mouse, rat, guinea pig, dog, cat, horse, cow, pig, monkey, chimpanzee, baboon, rhesus and non-human primates. In one embodiment, the subject is a mammal. In another embodiment, the subject is a human. In one embodiment, the term "subject" also encompasses any vertebrate including but not limited to mammals, reptiles, amphibians and fish.

A "cancer" or "tumor," as used herein, refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small noncleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin), anti-CD20 antibodies, an epidermal growth factor receptor (EGFR) antagonist (e.g., a tyrosine kinase inhibitor), HER1/EGFR inhibitor (e.g., erlotinib (Tarceva)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

BRIEF DESCRIPTION OF THE DRAWINGS

FIG. 3A shows the crystal structure of lactadherin C2 domain at 1.7 A resolution with mutational and computational analyses of its membrane-binding motif. (Shao et al. J Biol. Chem. 2008 283:7230-41). FIG. 3B demonstrates $Ca^{2+}$ independent PS binding by lactadherin according to Shi J. et al., Biochim. Biophysics. Acta 2004, 82-90.

FIG. 7 discloses, in the left column, SEQ ID NOS: 1-3, 40-41 and 4, and, in the right column, SEQ ID NOS: 42, 5-6, 44 and 7-8, respectively, in order of appearance.

FIG. 11A shows the backside stapling with click chemistry.

FIG. 11B shows the backside stapling with olefin metathesis.

FIG. 11C shows the synthesis of azido amino acids with varied side chain length. n=1-4; m=0-3.

DETAILED DESCRIPTION OF THE INVENTION

Unless otherwise explained, all technical and scientific terms used herein have the same meaning as commonly understood by one of ordinary skill in the art to which this disclosure belongs. Definitions of common terms in peptide chemistry may be found in "Peptide Chemistry: A Practical Textbook" by Miklos Bodanszky, published by Springer-Verlag, 2008 (ISBN-13: 978-0387189840), Current Protocols in Protein Science (Online ISBN: 9780471140863) ((John E. Coligan, et al. ed., John Wiley and Sons, Inc.), and Current Protocols in Molecular Biology (CPMB) (Fred M. Ausubel, et al. ed., John Wiley and Sons, Inc.). Unless otherwise stated, the peptides and uses thereof are made or performed respectively using standard procedures known to one skilled in the art, for example, in the referenced textbooks supra. Further, unless otherwise required by context, singular terms shall include pluralities and plural terms shall include the singular.

It should be understood that the peptides and uses thereof are not limited to the particular methodology, protocols, and reagents, etc., described herein and as such can vary. The terminology used herein is for the purpose of describing particular embodiments only, and is not intended to limit the scope of the peptides and uses thereof, which is defined solely by the claims.

All patents and other publications identified herein, both supra and infra, are expressly incorporated herein by reference for the purpose of describing and disclosing, for example, the methodologies described in such publications that could be used in connection with the peptides and methods described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Figure 4:
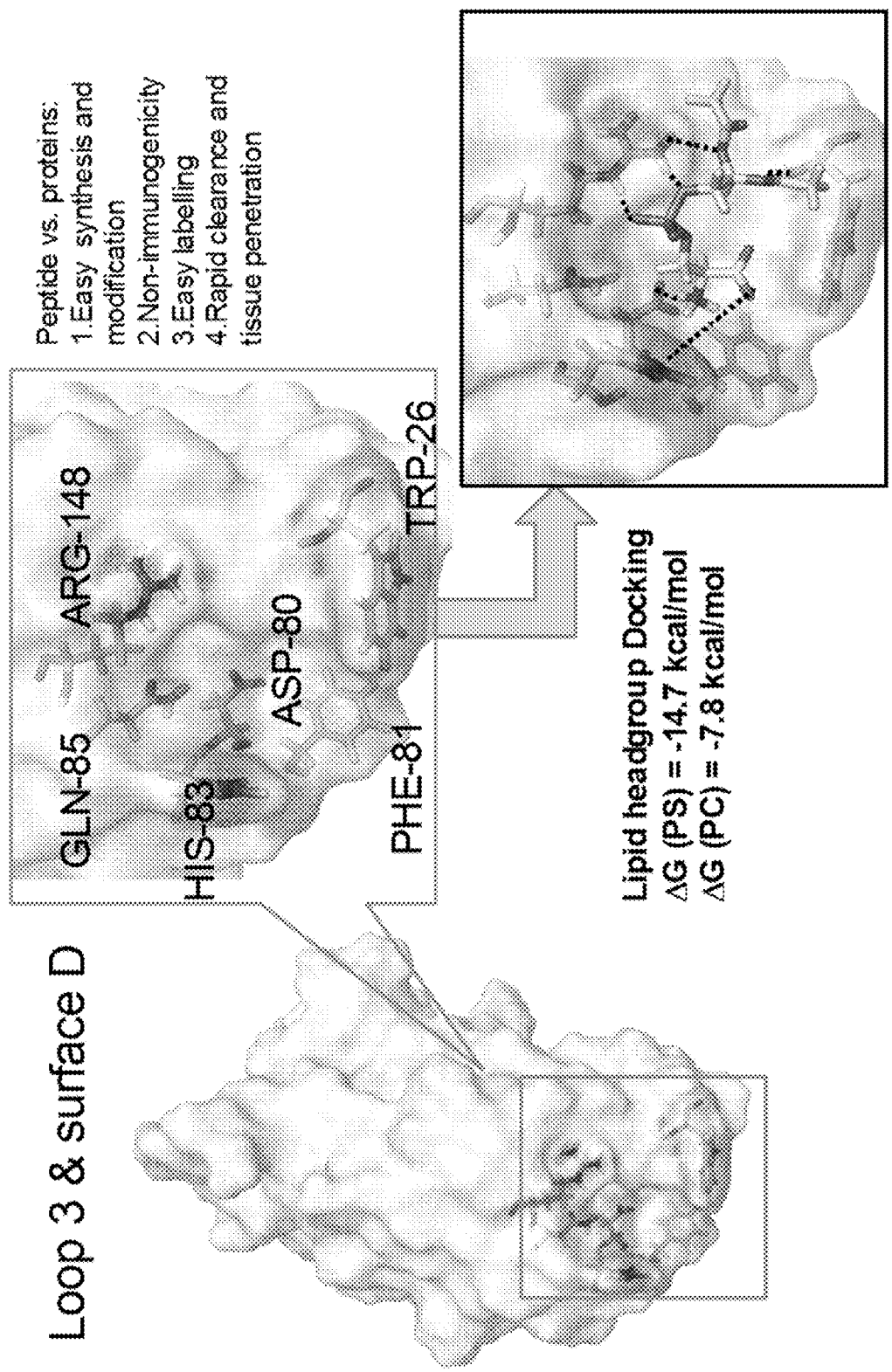
FIG. 4 shows the PS head group recognition by lactadherin.
Figure 5:
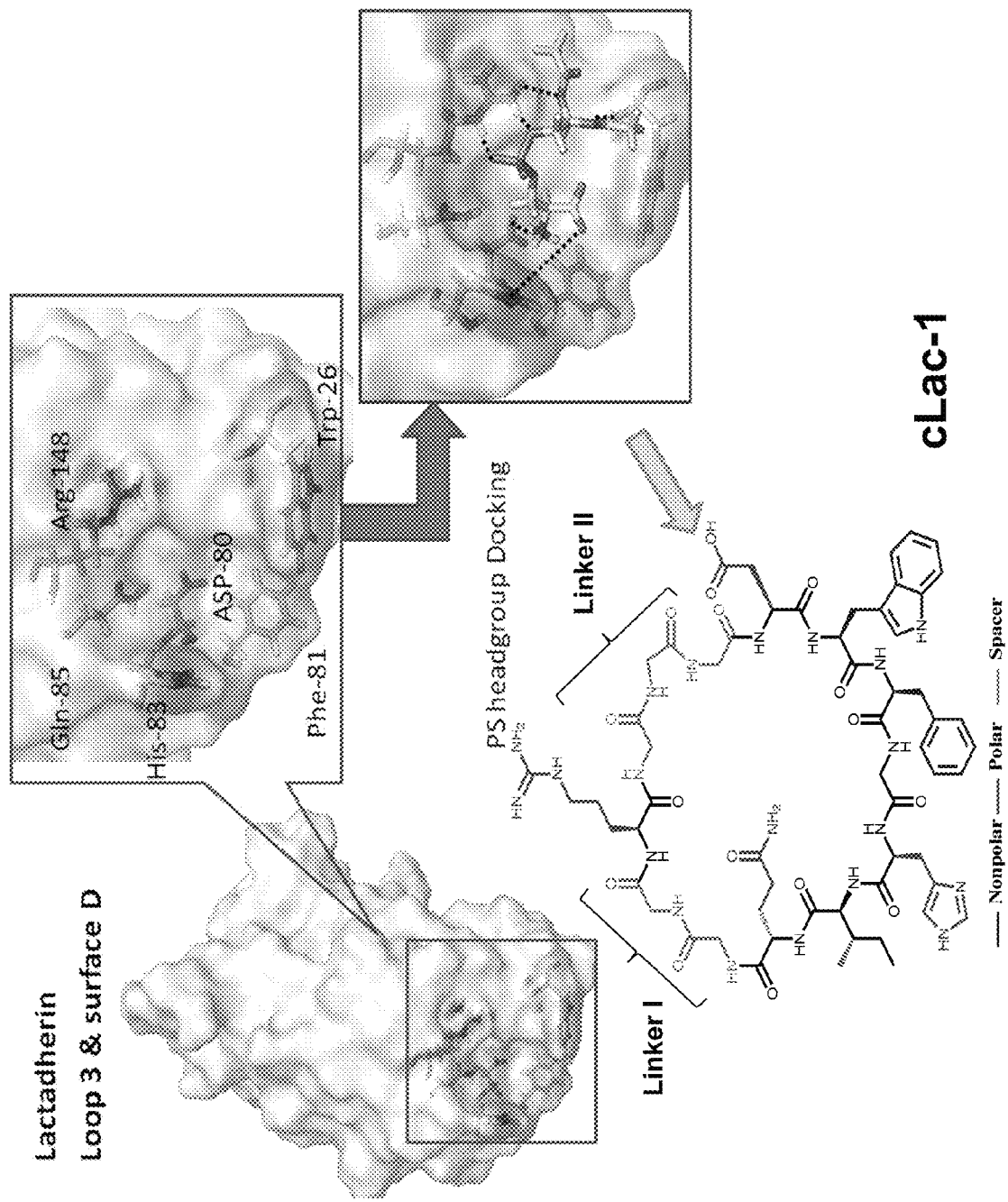
FIG. 5 shows structural modeling of Lact-C2 binding a short chain (diacetyl) PS, the design of a cyclic lactadherin peptide mimetic (cLac), cLac-1, that mimics the PS binding pocket of the Lact-C2 domain in lactadherin. cLac-1 is also known as Lac-Phe.

Embodiments of the invention described herein are based on the discovery that small synthetic cyclic peptide mimics of lactadherin have specific binding affinity to phosphatidylserine (PS) (see FIGS. 3 and 4), similar to the naturally occurring lactadherin and also similar to the PS binding domain in lactadherin, C2-domain (Lact-C2) (see FIG. 3). The cyclic peptide mimics are referred to as cyclic lactadherin mimics or cLacs. The inventors used synthetic peptide chemistry methods to make small cyclic peptides that mimic the PS binding pocket in lactadherin which contains the hydrophilic residues (Asp80, His83, Gln95 and Arg148) that engage in specific polar interactions with the PS headgroup (see FIGS. 4 and 5). In addition, the inventors incorporated the two consecutive hydrophobic residues in the design of the cLac for the purpose of insertion into the lipid membrane (FIGS. 5 and 6). The two consecutive hydrophobic residues mimic the Phe 81 and Trp 26 in lactadherin that are involved in docking on the cell membrane which is critical for PS binding (FIG. 5).

Accordingly, provided herein is a cyclic peptide (cLac) comprising at least 10 but no more than 20 amino acid residues having the formula I:

$$\boxed{A_1\text{-}A_2\text{-}A_{3(n)}\text{-}A_4\text{-}A_5\text{-}A_6\text{-}A_{7(x)}\text{-}A_8\text{-}A_{9(y)}\text{-}A_{10}}$$

wherein $A_1$ and $A_2$ are hydrophobic amino acid residues that are appropriate for lipid membrane binding, the side chains of these hydrophobic amino acid provide an added cLogP value of between 5 and 9, and wherein the hydrophobic amino acid residues are in the D or L configuration, are natural or unnatural amino acid, and are substituted or unsubstituted amino acid;

wherein $A_3$ is alanine or glycine, and n=1-3;

wherein $A_4$ is an amino acid with polar side chain that capable of strong hydrogen bonding or salt bridge;

wherein $A_5$ is a small hydrophobic amino acid;

wherein $A_6$ is an amino acid with polar side chain that capable of strong hydrogen bonding;

wherein $A_7$ and $A_9$ are neutral amino acid residues, and wherein x=1-5 and y=2-6;

wherein $A_8$ is a positively charged amino acid; and wherein $A_{10}$ is an amino acid with a negatively charged side chain.

In some embodiments of the cLac described herein, amino acid sequence modification(s) of the cyclic lactahedrin mimic described herein are contemplated. For example, it can be desirable to improve the binding affinity and/or other biological properties of the cyclic lactahedrin mimics. Such modified cyclic lactahedrin mimics are referred to as "cyclic lactahedrin mimic peptide variants" or "peptide variants." Amino acid sequence peptide variants of the cyclic lactahedrin mimics can be prepared by, for example, chemical peptide synthesis, which is a method known in the art. Such modifications include, for example, deletions from, and/or insertions into and/or substitutions of, residues within the amino acid sequences of the cyclic lactahedrin mimics. Any combination of one or more amino acid deletion, insertion, and substitution is made to arrive at the final peptide variant, provided that the final peptide variant possesses the desired characteristics, e.g., specifically binds to PS)

A useful method for identification of certain residues or regions of the cyclic lactahedrin mimics that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target, i.e., PS. Those amino acid locations demonstrating functional sensitivity to the substitutions then are refined by introducing further or other variants at, or for, the sites of substitution. Thus, while the site for introducing an amino acid sequence variation can be predetermined, the nature of the mutation per se need not be predetermined.

Amino acid sequence insertions include intra-sequence insertions of single or multiple amino acid residues. Another type of variant is an amino acid substitution variant. These variants have at least one amino acid residue in the cyclic lactahedrin mimic replaced by a different residue. In some embodiments, the substitution peptide variant is a conservative substitution.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (O); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. (See Table 1).

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Conservative amino acid substitutions do not change the overall structure of the peptide nor the type of amino acid side chains available for forming van der Waals bonds with a binding partner. Conservative amino acid substitution can be achieved during chemical synthesis of the peptide by adding the desired substitute amino acid at the appropriate sequence in the synthesis process. Alternatively, molecular biology methods can be used. The coding sequence of a peptide described herein can be made by annealing two single strand nucleic acids that are complementary to each other. Alternatively, site-directed mutagenesis can be used for conservative amino acid substitution in the peptides described herein. Methods of chemical peptide synthesis, molecular biology methods for production of peptides, and site-directed mutagenesis are known in the art.

In one embodiment, "amino acid" of a cLac peptide refers to naturally occurring amino acids. In another embodiment, "amino acid" refers to synthetic amino acids. In other embodiment, "amino acid" refers to amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

In some embodiments, all amino acids of cLac i.e., amino acid residues at position $A_1$, $A_2$, $A_3$, $A_4$, $A_5$, $A_6$, $A_7$, $A_8$, $A_9$, and $A_{10}$ are in the D- or L configuration.

Figures 16A, 16B:
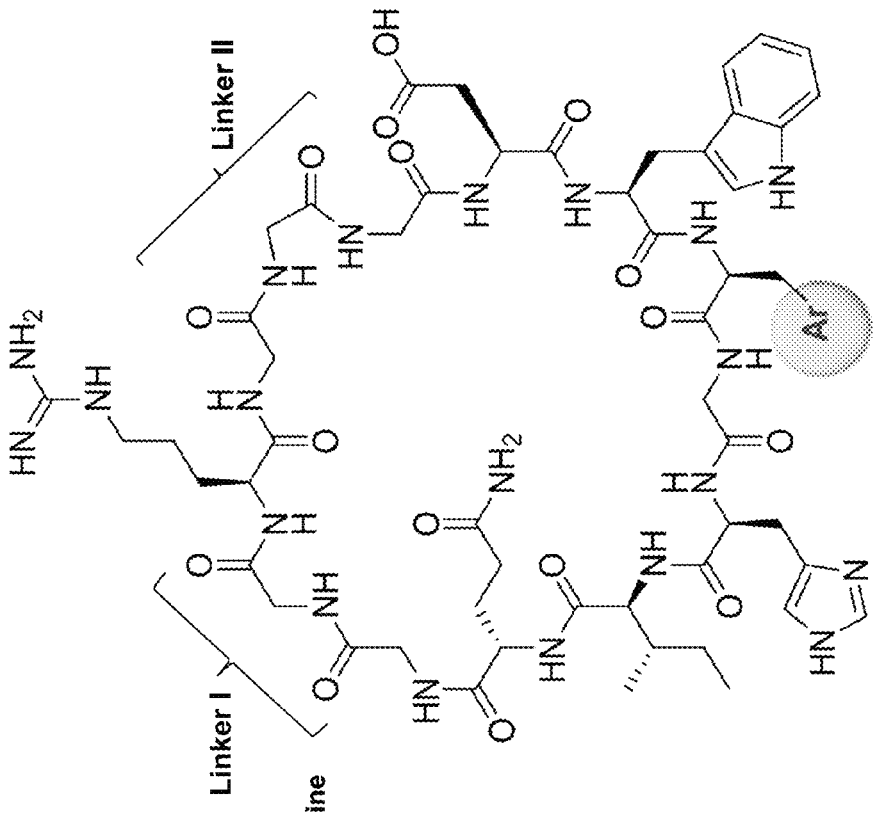
FIG. 16A shows a variety of side chains of unnatural amino acids that can occupy the A2 hydrophobic motif to confer PS-selective membrane insertion of the cLac peptide variants.
FIG. 16B shows the location of the side chain of the A2 hydrophobic residue that contributes to PS-selective membrane insertion activity.

In some embodiments, there can be modifications or derivations of the α, β, or γ position in the amino acids of the cLac. In some embodiments, the modifications or derivations of the α, β, or γ position can be those shown in the FIG. 16A. In some embodiments, the modifications or derivations of the α, β, or γ position can be any one of a halogenated aromatic group, a halogenated aliphatic group, an aliphatic group and an aromatic group.

In some embodiments, the amino acids of cLac can be natural or unnatural amino acids. Unnatural amino acids are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids.

In some embodiments, the amino acids of cLac can be substituted or unsubstituted. The substituted amino acid or substituent is a halogenated aromatic or aliphatic amino acid, a halogenated aliphatic or aromatic modification on the hydrophobic side chain, or an aliphatic or aromatic modification.

In some embodiments, one can also substitute a particular residue to enhance the binding to the detectable moiety, i.e., PS exposed on the cell surface membrane.

In one embodiment, $A_1$ and $A_2$ are hydrophobic amino acid residues such as alanine, glycine, histidine, proline, serine, threonine, tyrosine, cysteine, methionine, valine, tryptophan, phenylalanine, leucine, isoleucine, biphenylalanine, methylphenylalanine, and terphenylalnine. In one embodiment, the residues at positions $A_1$ and $A_2$ can be substituted by any consecutive hydrophobic amino acid residues.

In one embodiment, the hydrophobic amino acid residues combine to form a hydrophobic motif that is responsible for the peptide insertion into lipid membranes. Accordingly, the cLac comprises a hydrophobic motif for lipid membrane insertion.

In one embodiment, the two $A_1$ and $A_2$ residues constitute the hydrophobic motif for lipid membrane binding. In another embodiment, only $A_1$ or only $A_2$ residue constitutes the hydrophobic motif for lipid membrane binding.

In one embodiment, the hydrophobic motif consists of one or two hydrophobic amino acid residues with an added hydrophobicity appropriate for membrane binding.

As used herein "added hydrophobicity appropriate for membrane binding" refers to having a cLogP value of between 5 and 9. The value of ClogP tells you how hydrophobic a molecule is. The higher the ClogP value, the more hydrophobic the molecule is. For example, a very hydrophilic molecule has a ClogP=−6, intermediate molecule has a ClogP=0, and very hydrophobic molecule has ClogP=+6. Methods of calculating ClogP are known in the art, e.g., the OSIRIS Property Explorer program available at the Organic Chemistry Portal and the ClogP manual available from Daylight Chemical Information Systems, Inc.

In one embodiment, the cLac has a motif suitable for inserting into lipid membrane. For example, a two-hydrophobic amino acid motif that results in a cLogP value of between 5 and 9. For example, a two-hydrophobic amino acid motif which when present in cLac permits liposome binding as analyzed by the Trp-to-dansyl FRET assay described herein.

The hydrophobic or hydrophilic nature of an amino acid side chain generally correlates with its non-polar or polar character, with non-polar amino acids generally recognized as being hydrophobic, and polar amino acids being recognized as hydrophilic. However, the individual non-polar amino acids have varying degrees of hydrophobicity. In one embodiment, the amino acid side chain of $A_1$ and/or $A_2$ is selected from the group consisting of p-phenyl-L-phenylalanine, 3-(2-naphthyl)-L-alanine, 3-(1-naphthyl)-L-alanine, 4-Iodo-L-phenylalanine, 4-tert-butyl-L-phenylalanine, 4-Bromo-L-phenylalanine, 3,4,5-Trifluoro-L-phenylalanine, tryptophan and pentafluoro-L-phenylalanine.

A scale of hydrophilicity/hydrophobicity based on the free energy of hydrophobic association is described, for example, by Urry, D. W. (2004), "The change in Gibbs free energy for hydrophobic association—Derivation and evaluation by means of inverse temperature transitions," Chemical Physics Letters 399 (1-3): 177-183, which is incorporated herein by reference in its entirety.

The hydropathy index of an amino acid is a number representing the hydrophobic or hydrophilic properties of its sidechain. It was proposed in 1982 by Jack Kyte and Russell Doolittle (J. Mol. Biol. 157: 105-32). The larger the number is, the more hydrophobic the amino acid. The most hydrophobic amino acids are isoleucine (4.5) and valine (4.2). The most hydrophilic ones are arginine (−4.5) and lysine (−3.9). The hydropathy index for the twenty naturally occurring amino acids according to Kyte and Doolittle is provided in Table 1.

In one embodiment, the amino acid residues at $A_1$ and/or $A_2$ are the D-configuration.

The binding of cLac to lipid membrane can be analyzed by any method known it the art. For example, by the fluorescence assay (Trp-to-dansyl FRET) described herein. Basically, large unilamellar vesicles (100 nm in diameter) were prepared with phosphatidylcholine (PC) and varied percentages of PS. All vesicles contained 5% dansyl-labeled PE to serve as a reporting group. The peptide-vesicle binding was monitored by the fluorescence resonance energy transfer (FRET) from Trp to the dansyl group. Emission of sensitized dansyl is monitored at 520 nm and Trp emission is monitored near 350 nm. Membrane binding of cLac to the PC/PS vesicles produces a sensitized dansyl emission at 520 nm with a concurrent decrease of Trp emission near 350 nm.

In one embodiment, the hydrophobic motif consists of two hydrophobic amino acid residues which are tryptophan (W) and biphenylalanine (Bip). In this embodiment, the orientation of the two consecutive hydrophobic amino acid residues can be either tryptophan (W) followed by biphenylalanine (Bip) or biphenylalanine (Bip) followed by tryptophan (W).

In one embodiment, $A_1$ is tryptophan (W) and $A_2$ is biphenylalanine (Bip)

In another embodiment, $A_1$ is biphenylalanine (Bip) and $A_2$ is tryptophan (W).

In one embodiment, the hydrophobic motif consists of two hydrophobic amino acid residues, one of which is tryptophan (W) and the other is not phenylalanine (F).

In one embodiment, $A_1$ is tryptophan (W) and $A_2$ is not phenylalanine (F).

In another embodiment, $A_1$ is not phenylalanine (F) and $A_2$ is tryptophan (W).

In one embodiment, the hydrophobic motif consists of two hydrophobic the amino acid residues wherein at least one of which is tryptophan (W).

In one embodiment, $A_1$ is tryptophan (W). In another embodiment, $A_2$ is tryptophan (W).

In one embodiment, the hydrophobic motif consists of two hydrophobic amino acid residues wherein at least one of which is biphenylalanine (Bip). It is contemplated that Bip can be at either position $A_1$ or $A_2$.

In one embodiment, $A_1$ is tryptophan (W) and $A_2$ is not glycine (G). In one embodiment, $A_2$ is tryptophan (W) and $A_1$ is not glycine (G).

In one embodiment, $A_1$ is tryptophan (W) and $A_2$ is not terphenylalnine (Tph). In one embodiment, $A_2$ is tryptophan (W) and $A_1$ is not terphenylalnine (Tph).

In one embodiment, the hydrophobic motif consists of two hydrophobic amino acid residues wherein at least one amino acid has a side chain substituted with naphthalene at the 1-(Np-1) or 2-(Np-2) position (see FIG. 16).

In some embodiments, the amino acids include but are not limited to the natural residues (tryptophan, phenylalanine, leucine, isoleucine), as well as neutral unnatural residues, i.e., substitutions in the aromatic and aliphatic amino acid. The substitutions include but not limited to halogenation of amino acids to give fluorinated aromatic/aliphatic amino acids; aliphatic/aromatic modifications on hydrophobic side chain at different positions or numbers, such as methyl-phenylalanine, terphenylalnine etc.

In one embodiment, the aliphatic modification on the hydrophobic side chain is between 1 to 10 carbons, 1 to 6 carbons, or 1 to 4 carbons, and wherein the aliphatic modification is straight chain alkyl or alkenyl.

In some embodiments, the amino acids other than those comprising the hydrophobic motif $A_1$ and $A_2$ are natural amino acids.

In some embodiments, the amino acid residues other than the hydrophobic motif and the spacer (e.g., $A_3$, $A_7$ $A_9$) are natural amino acids.

In one embodiment, the $A_3$, $A_7$ and $A_9$ residues function as spacer amino acids designed to link $A_2$ to $A_4$, $A_6$-$A_8$ and $A_8$-$A_{10}$ in the cLac respectively. Spacer residues offer a degree of freedom that other residues do not. The key factor is that they, the spacer residues, do not adversely affect the overall conformation or change the cyclic peptide, and also they do not adversely affect the activity of the cyclic peptide, i.e. the specific PS binding and lipid membrane binding. There can be anywhere from one to three $A_3$ residues, one to five $A_7$ residues and two to six $A_9$ residues. It is contemplated that any neutral amino acid residues will be suitable. In some embodiments, $A_3$, $A_7$ and $A_9$ are each individually selected from the group consisting of glycine, alanine, valine, leucine, isoleucine, cysteine, tyrosine, tryptophan, serine, threonine, proline, methionine, phenylalanine, glutamine, asparagine and propargyl glycine (PPG). All possible combinations of neutral amino acid residues is contemplated for $A_3$, $A_7$ and $A_9$ when there are multiple $A_3$, $A_7$ or $A_9$ residues in the cLac.

In one embodiment, $A_3$, $A_7$, and/or $A_9$ are glycine (G).

In one embodiment, $A_3$, $A_7$, and/or $A_9$ are alanine (A)

In some embodiments, there are one $A_3$, two $A_3$ or three $A_3$ residues in the cyclic cLac peptide.

In the embodiments where there are multiple $A_3$ residues, the $A_3$ residues are all identical neutral amino acids, e.g., all glycines or all alanines.

In one embodiment, there is one $A_7$.

In other embodiments, there are two $A_7$, three $A_7$, four $A_7$ or five $A_7$ residues in the cLac.

In one embodiment, there are two $A_7$ residues which are GG, GA, or AG.

In other embodiments, there are two $A_7$ residues which selected from the group consisting of AA, VV, II, LL, CC, SS, TT, WW, YY, PP, FF, MM, QQ and NN.

In the embodiments where there is more than one $A_7$ residue, the $A_7$ residues have identical neutral amino acid residues. For example, GG, AA, GGG, AAA, VVV, GGGG (SEQ. ID. NO:13), AAAA (SEQ. ID. NO:)14, IIII (SEQ. ID. NO:15), and VVVVV (SEQ. ID. NO:16).

In the embodiments where there is more than one $A_7$ residue, the $A_7$ residues are various combinations of neutral amino acid residues thereof. For example, GA, AA, GV, GAG, AVAV (SEQ. ID. NO:17), VAV, GIGV (SEQ. ID. NO:18), CAVA (SEQ. ID. NO:19), GIIIG (SEQ. ID. NO:20) and VGVAV (SEQ. ID. NO:21).

In one embodiment, there is one $A_9$ residue.

In other embodiments, there are two $A_9$, three $A_9$, four $A_9$, five $A_9$ or six $A_9$ residues in cLac.

In one embodiment, there are four $A_9$ residues which are GGGG (SEQ. ID. NO:13).

In other embodiments, there are four $A_9$ residues which selected from the group consisting of AAAA (SEQ. ID. NO:14), VVVV (SEQ. ID. NO:22), IIII (SEQ. ID. NO:23), LLLL (SEQ. ID. NO:24), CCCC (SEQ. ID. NO:25), SSSS (SEQ. ID. NO:26), TTTT (SEQ. ID. NO:27), WWWW (SEQ. ID. NO:28), YYYY (SEQ. ID. NO:29), PPPP (SEQ. ID. NO:30), FFFF (SEQ. ID. NO:31), MMMM (SEQ. ID. NO:32), QQQQ (SEQ. ID. NO:33) and NNNN (SEQ. ID. NO:34).

In the embodiments where there is more than one $A_9$ residue, the $A_9$ residues are all identical neutral amino acid residues. For example, GG, AA, GGG, AAA, VVV, GGGG (SEQ. ID. NO:13), AAAA (SEQ. ID. NO:14), IIIII (SEQ. ID. NO:15) and VVVVV (SEQ. ID. NO:16).

In the embodiments where there is more than one $A_9$ residue, the $A_9$ residues are any possible combinations of neutral amino acid residues thereof. For example, GA, AA, GV, GAG, AVAV (SEQ. ID. NO:17), VAV, GIGV (SEQ. ID. NO:18), CAVA (SEQ. ID. NO:19), GIIIG (SEQ. ID. NO:20) and VGVAV (SEQ. ID. NO:21).

In one embodiment, any one of the neutral amino acid of e.g., $A_3$, $A_7$ or $A_9$ is an unnatural amino acid or derivatives thereof. Unnatural amino acid or derivatives are well known in the art, e.g., see the website of SIGMA ALDRICH and U.S. Pat. No. 7,045,337. In one embodiment, the unnatural neutral amino acid has a modification to the side chain, e.g., propargyl glycine (PPG). In one embodiment, the modification to the side chain of the unnatural neutral amino acid functions to make a linkage bond with other molecules or with an intramolecular cLac amino acid residue. For example, linking with a detectable label such as a fluorescent label or an internal linking with another neutral spacer amino acid within the cLac molecule (i.e., intramolecular cLac amino acid residue). In one embodiment, the intramolecular cLac amino acid residue is a neutral spacer amino acid. In one embodiment, the intramolecular cLac amino acid residue is a neutral spacer amino acid in the $A_3$, $A_7$ or $A_9$ position. In one embodiment, the unnatural neutral amino acid and the intramolecular cLac amino acid residue used for linkage bond formation are not in the same spacer position. That is to say that when the unnatural neutral amino acid and the intramolecular cLac amino acid residue forms a linkage, e.g., described in "backside" stapling, both the amino acid residues are not found in $A_3$, $A_7$ or $A_9$. Ideally, the unnatural neutral amino acid and the intramolecular cLac amino acid residue that forms a linkage are on opposite half of the cyclic peptide.

As used herein, an "intramolecular cLac amino acid residue" is an amino acid residue within a cyclic peptide of Formula I.

In some embodiments of the aspects described herein, a cLac further comprises internal linkage(s) between the amino acids of the cyclic peptide in addition to the standard peptide linkages. In some embodiments, the internal linkages are extra linkages that function to stabilize the cyclic peptide. In some embodiments, the internal linkages are "backside stapling" linkages. In some embodiments, the backside stapling linkages are not between two adjacent amino acids in the cyclic peptide. In some embodiments, the backside stapling linkages are between two amino acids that are approximately opposite each other in the cyclic peptide, i.e. across from each other. In some embodiments, the backside stapling linkages are between two amino acids that on two opposite halves of the cyclic peptide. In some embodiments, the backside stapling linkages are between two amino acids that are separated from each other by at least three amino acids in the cyclic peptide. In other embodiments, two amino acids that are separated from each other by at least four amino acids, at least five amino acids, at least six amino acids, at least seven amino acids, at least eight amino acids, at least nine amino acids, and at least ten amino acids in the cyclic peptide. In some embodiments, the backside stapling linkages are not between two adjacent amino acids in the cyclic peptide. In one embodiment, the backside stapling linkages in between one amino acid in the $A_3$ position and the other amino acid in the $A_7$ position. In some embodiments, other combinations include $A_3$ position-$A_9$ position backside stapling and $A_7$ position-$A_9$ position backside stapling. In other embodiments, it is contemplated that backside stapling can involve the amino acid at position $A_5$, and also involve the optional spacer amino acid(s) between $A_1$ and $A_{10}$.

In one embodiment, there is at least one unnatural neutral amino acid with a modification to the side chain in the spacer positions $A_3$, $A_7$ and/or $A_9$. In another embodiment, there is only one unnatural neutral amino acid with a modification to the side chain in the spacer positions $A_3$, $A_7$ and/or $A_9$. In other embodiment, the unnatural neutral amino acid with a modification to the side chain in the spacer positions $A_3$, $A_7$ and/or $A_9$ are different at each spacer position within a cLAc.

In one embodiment, $A_4$ is an amino acid with polar side chains that capable of strong hydrogen bonding or salt bridges. In one embodiment, $A_4$ forms a hydrogen bond or a salt bridge when protonated with the PS headgroup.

In one embodiment, $A_4$ is selected from the group consisting of histidine, asparagine, glutamine, lysine, arginine, its analogues and derivatives (e.g., 2-amino-3-guanidinopropionic acid, 2-amino-4-guanidino-butyric acid and 2-amino-6-guanidinocaproic acid (see the website of SIGMA ALDRICH and Iris-Biotech GMBH).

In one embodiment, $A_4$ is histidine.

In one embodiment, $A_5$ is small hydrophobic amino acid.

In one embodiment, $A_5$ is selected from the group consisting of isoleucine, alanine, valine, leucine and methionine.

In other embodiment, $A_5$ is isoleucine.

In one embodiment, $A_6$ forms a hydrogen bond with phosphatidylserine headgroup.

In one embodiment, $A_6$ is an amino acid with polar side chains that capable of strong hydrogen bonding, e.g., from 10 to >155 kJ mol$^{-1}$.

In one embodiment, $A_6$ is selected from the group consisting of glutamine, tyrosine, serine, asparagine, histidine, cysteine and threonine.

In one embodiment, $A_6$ is glutamine.

In one embodiment, $A_6$ is an unnatural amino acid that contains hydrogen bond donating/accepting motif on the side chain.

In one embodiment, $A_8$ is a positively charged amino acid. In one embodiment, A8 is not limited by variation of side chain length.

In one embodiment, $A_8$ is responsible for the specific recognition of PS through salt bridge formation to target the negatively charged phosphate on the PS headgroup.

In one embodiment, $A_8$ is selected from the group consisting of lysine, arginine and the analogues and derivatives of these amino acids (e.g., ornithine, 2,4-diaminobutanoic acid, and 2,3-diaminopropanoic acid, 2-amino-3-guanidinopropionic acid, 2-amino-4-guanidino-butyric acid and 2-amino-6-guanidinocaproic acid.

In one embodiment, $A_8$ is arginine.

In one embodiment, $A_{10}$ is an amino acid with a negatively charged side chain.

In one embodiment, $A_{10}$ is not limited by variation of side chain length of the amino acid.

In one embodiment, $A_{10}$ is responsible for the specific recognition of phosphatidylserine through salt bridge formation to interact with the positively charged ammonium group of PS.

In another embodiment, $A_{10}$ is selected from a group consisting of aspartic acid, glutamic acid and the analogues and derivatives of these amino acids (e.g., described in EPO Patent EP0656345).

In one embodiment, $A_{10}$ is aspartic acid.

In one embodiment, there is another spacer amino acid(s) between $A_1$ and $A_{10}$. In one embodiment, spacer amino acid(s) between $A_1$ and $A_{10}$ is similar to those of the spacer amino acids in position $A_3$, $A_7$ and $A_9$. In one embodiment, spacer amino acid(s) between $A_1$ and $A_{10}$ is a neutral amino acid. In one embodiment, spacer amino acid(s) between $A_1$ and $A_{10}$ is selected from the group consisting of glycine, alanine, valine, leucine, isoleucine, cysteine, tyrosine, tryptophan, serine, threonine, proline, methionine, phenylalanine, glutamine, asparagine and propargyl glycine (PPG). Similar to the $A_3$, $A_7$ and $A_9$ residues, spacer amino acid(s) between $A_1$ and $A_{10}$ can be an unnatural amino acid and/or for the purpose of forming linkages with other molecules or intramolecular cLac amino acid residue.

In one embodiment, the cLac binds to PS. Methods for analyzing specific PS binding are known in the art. For example, as described by Thapa N. et al., 2008, J. Cell Mel. Med. 12: 1649-1660 and the Trp-to-dansyl FRET fluorescence method using PC/PS vesicles described herein.

In one embodiment of any one of cLac described, the cLac binds lipid membranes.

In one embodiment of any one of cLac described, any of the amino acid can be in either the D- or L-configuration.

Methods of synthesis of cyclic peptides are well known in the art. For example, see U.S. Pat. Nos. 5,990,273, 7,582,728, 7,563,865, EP0518295, PCT US08/56609, WO/2011/048029 and WO 90/05738, and US Patent application No: 20090215172. These patents and publications are expressly incorporated herein by references. Peptides described herein can be synthetically constructed by suitable known peptide polymerization techniques, such as exclusively solid phase techniques, partial solid-phase techniques, fragment condensation or classical solution couplings. For example, the peptides of the invention can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859. Other available syntheses are exemplified in U.S. Pat. Nos. 3,842,067, 3,872,925, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego. #9830). The foregoing disclosures are incorporated herein by reference.

Methods for stabilizing peptides known in the art may be used with the cyclic peptides, methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety.

In one embodiment, the cLac is stabilized by backside stapling as described herein. In one embodiment, the cLac is stabilized by any method known in the art provided that the stabilized cLac retains activity, i.e., lipid membrane binding and specific PS binding.

Encompassed by the cLac peptide described herein are chemical derivatives of a peptide whose amino acid residue sequence is described herein, so long as they substantially retain the activities of those peptides, i.e., lipid membrane binding and/or PS binding. A "chemical derivative" is a subset of peptide derivatives as described herein and refers to a subject polypeptide having one or more residues chemically derivatized by reaction of a functional side group. In addition to side group derivatizations, a chemical derivative can have one or more backbone modifications including alpha-amino substitutions such as N-methyl, N-ethyl, N-propyl and the like, and alpha-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. Also included as chemical derivatives are those peptides which contain one or more non-limiting, non-natural amino acids, examples include those available for peptide synthesis from commercial suppliers (e.g. Bachem Catalog, 2004 pp. 1-276). For examples: 4-hydroxyproline may be substituted for proline; 5-hydroxylysine may be substituted for lysine; 3-methylhistidine may be substituted for histidine; homoserine may be substituted for serine; ornithine may be substituted for lysine; β-alanine may be substituted for alanine; norleucine may be substituted for leucine; phenylglycine may be substituted for phenylalanine, and L-1,2,3,4-tetrahydronorharman-3-carboxylic acid or H-β-(3-Benzothienyl)-Ala-OH may be substituted for tryptophan.

In certain embodiments, chemical modifications to the peptide include, but are not limited to the inclusion of, alkyl, alkoxy, hydroxyalkyl, alkoxyalkyl, alkoxycarbonyl, alkenyl, alkynyl, cycloalkyl, amino, alkylamino, aminoalkyl, dialkylamino, aminodialkyl, halogen, heteroatom, carbocycle, carbocyclyl, carbocyclo, carbocyclic, aryl, aralkyl, aralkoxy, aryloxyalkyl, heterocycle, heterocyclyl, heterocyclic, heteroaryl, and/or aliphatic groups.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C3-C12 hydrocarbons which are completely saturated or which contain one or more units of unsaturation, but which are not aromatic. Lower alkyl refers to an alkyl group containing 1-6 carbons.

The term "amino" refers to an $NH_2$ group.

The term "alkylamino" or "aminoalkyl" refers to an amino group wherein one of the hydrogen atoms is replaced by an alkyl group.

The term "dialkylamino" or "aminodialkyl" refers to an amino group wherein the hydrogen atoms are replaced by alkyl groups, wherein the alkyl group may be the same or different.

The term "halogen" means F, Cl, Br, or I.

The term "heteroatom" means nitrogen, oxygen, or sulfur with a carbon ring structure and includes any oxidized form of nitrogen and sulfur, and the quaternized form of any basic nitrogen. Also the term "nitrogen" includes substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+(as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having six to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetrahydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on any unsaturated carbon atom of an aryl, heteroaryl, aralkyl, or heteroaralkyl group include a halogen, —R0, —OR0, —SR0, 1,2-methylene-dioxy, 1,2-ethylenedioxy, protected OH (such as acyloxy), phenyl (Ph), substituted Ph, —O(Ph), substituted —O(Ph), —CH2(Ph), substituted —CH2(Ph), CH2CH2 (Ph), substituted —CH2CH2(Ph), —NO2, —CN, —N(R0)2, —NR0C(O)R0, NR0C(O)N(R0)2, NR0CO2R0, —NR0NR0C(O)R0, —NR0NR0C(O)N(R0)2, —NR0NR0C2R0, C(O)C(O)R0, C(O)CH2C(O)R0, —CO2R0, —C(O)R0, —C(O)N(R0)2, —OC(O)N(R0)2, S(O)2R0, —SO2N(R0)2, —S(O)R0, —NR0SO2N(R0)2, —NR0SO2R0, —C(=S)N(R0)2, C(=NH)N(R0)2, (CH2) yNHC(O)R0, and —(CH2)yNHC(O)CH(V—R0)(R0); wherein each R0 is independently selected from hydrogen, a substituted or unsubstituted aliphatic group, an unsubstituted heteroaryl or heterocyclic ring, phenyl (Ph), substituted Ph, O(Ph), substituted —O(Ph), —CH2 (Ph), or substituted —CH2(Ph); y is 0-6; and V is a linker group. Examples of substituents on the aliphatic group or the phenyl ring of R0 include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

An aliphatic group or a non-aromatic heterocyclic ring or a fused aryl or heteroaryl ring may contain one or more substituents. Examples of suitable substituents on any saturated carbon of an aliphatic group or of a non-aromatic heterocyclic ring or a fused aryl or heteroaryl ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group, or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

Suitable substituents on the nitrogen of a non-aromatic heterocyclic ring include R+, —N(R+)$_2$, —C(O)R+, —CO$_2$R+, —C(O)C(O)R+, —C(O)CH$_2$C(O)R+, —SO$_2$R+, —SO$_2$N(R+)$_2$, C(=S)N(R+)$_2$, —C(=NH)—N(R+)$_2$, and —NR+SO$_2$R+; wherein each R+ is independently selected from hydrogen, an aliphatic group, a substituted aliphatic group, phenyl (Ph), substituted Ph, —O(Ph), substituted —O(Ph), —CH$_2$(Ph), substituted —CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

In one embodiment, the cLac comprising a linker molecule or linker moiety.

In one embodiment, the cLac further comprising a label. In another embodiment, the label in a detectable label.

In one embodiment, the cLac label is a fluorescent label, a magnetic resonance imaging (MRI) contrast label, computed tomography (CT) contrast label or positron emission tomography (PET) imaging label.

In certain embodiments, the cLac comprises at least one linker moiety for a covalent attachment to a label. (See FIG. 13). The linker moiety is preferably, although not necessarily, a $C_{1-12}$ linking moiety optionally terminated with one or two —NH— linkages and optionally substituted at one or more available carbon atoms with a lower alkyl substituent. In one embodiment, the linker comprises —NH—R—NH— wherein R is a lower ($C_{1-6}$) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue.

In one embodiment, the linker moiety is a $C_{1-12}$ linking moiety optionally terminated with —NH— linkages or carboxyl (—COOH) groups, and optionally substituted at one or more available carbon atoms with a lower alkyl substituent. In one embodiment, the linker is R—COOH wherein R is a lower ($C_{1-6}$) alkyl optionally substituted with a functional group such as a carboxyl group or an amino group that enables binding to another molecular moiety. For example, the linker may be a glycine (G) residue, or an amino hexanoic acid (Ahx) such as 6-amino hexanoic acid. In other embodiments, the linker is —NH—R—NH— wherein R is a lower ($C_{1-6}$) alkyl substituted with a functional group such as a carboxyl group or an amino group that enables binding to another molecular moiety. For example, the linker may be a lysine (K) residue or a lysine amide (K—NH$_2$, a lysine residue wherein the carboxyl group has been converted to an amide moiety —CONH$_2$).

In some embodiments, the linker moiety has the following structure: —NH—(CH$_2$)$_\alpha$—[O—(CH$_2$)$_\beta$]$_\gamma$—O$_\delta$—(CH$_2$)$_\epsilon$—Y— where the $\alpha$, $\beta$, $\gamma$, $\delta$, and $\epsilon$ are each integers whose values are independently selected. In some embodiments, $\alpha$, $\beta$, and $\epsilon$ are each integers whose values are independently selected between one and about six, $\delta$ is zero or one, $\gamma$ is an integer selected between zero and about ten, except that when $\gamma$ is greater than one, $\beta$ is two, and Y is selected from NH or CO. In some embodiments, the $\alpha$, $\beta$, and $\epsilon$ are each equal to two, both $\gamma$ and $\delta$ are equal to 1, and Y is NH. In another embodiment, $\gamma$ and $\delta$ are zero, $\alpha$ and $\epsilon$ together equal five, and Y is CO.

In one embodiment, the linking moiety is a peptide linker A "peptide linker" is a short (e.g., about 1-40, e.g., 1-20 amino acids) sequence of amino acids that is not part of the peptide or variant sequence described herein. A linker peptide is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers (e.g., a (Gly4Ser)n (SEQ ID NO: 45) repeat where n=1-8, preferably, n=3, 4, 5, or 6). The cLac peptide-lable conjugate described herein can also be joined by chemical bond linkages, such as linkages by disulfide bonds or by chemical bridges. Molecular biology techniques that are well known to those skilled in the art can be used to create a polymer of peptides. In one embodiment, combination of a peptide and variant peptide is found in the polymer. cLac peptide sequences of the present invention can also be linked together using non-peptide cross-linkers (Pierce 2003-2004 Applications Handbook and Catalog, Chapter 6) or other scaffolds such as HPMA, polydextran, polysaccharides, ethylene-glycol, poly-ethylene-glycol, glycerol, sugars, and sugar alcohols (e.g. sorbitol, mannitol).

In an optional embodiment, polyethylene glycol (PEG) may serve as a linker that dimerizes two peptide monomers: for example, a single PEG moiety containing two reactive functional groups may be simultaneously attached to the N-termini of both peptide chains of a peptide dimer. These peptides are referred to herein as "PEGylated peptides."

In yet another embodiment, a linker moiety may comprise a molecule containing two carboxylic acids and optionally substituted at one or more available atoms with an additional functional group such as an amine capable of being bound to one or more PEG molecules. Such a molecule can be depicted as: —CO—(CH$_2$)n-uX—(CH$_2$)m-CO— where n is an integer between zero and 10, m is an integer between one and 10, X is selected from O, S, N(CH$_2$)pNR1, NCO(CH$_2$)pNR1, and CHNR1, R1 is selected from H, Boc (tert-butyloxycarbonyl), Cbz, and p is an integer between 1 and 10. In certain embodiments, one amino group of each of the peptides forms an amide bond with the linker. In certain other embodiments, the amino group of the peptide bound to the linker is the epsilon amine of a lysine residue or the alpha amine of the N-terminal residue, or an amino group of an optional spacer molecule. In one embodiment, a linker is used to cyclize peptides. In another embodiment, a spacer can be used in addition to a linker molecule for separating moieties as desired. In particularly preferred embodiments, both n and m are one, X is NCO(CH$_2$)pNR1, p is two, and R1 is Boc. Optionally, the Boc group can be removed to liberate a reactive amine group capable of forming a covalent bond with a suitably activated PEG species such as mPEG-SPA-NHS or mPEG-NPC (Nektar Therapeutics, San Carlos Calif.). Optionally, the linker contains more than one reactive amine capable of being derivatized with a suitably activated PEG species. Optionally, the linker contains one or more reactive amines capable of being derivatized with a suitably activated pharmacokinetic (PK) modifying agent such as a fatty acid, a homing peptide, a transport agent, a cell-penetrating agent, an organ-targeting agent, or a chelating agent.

In one embodiment, the cLac is linked to the label by a chelating agent. A variety of chelating agents can be used to conjugate the label to the cLac peptides described herein. These chelating agents include but are not limited to ethylenediaminetetraacetic acid (EDTA), diethylenetriaminepentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et al, 1978, Nature 271, 752-755; Harokopakis E., et. al., 1995, Journal of Immunological Methods, 185:31-42; S. F. Atkinson, et al., 2001, J. Biol. Chem., 276:27930-27935; and U.S. Pat. Nos. 5,601,825, 5,180,816, 6,423,685, 6,706,252, 6,884,780, and 7,022,673, which are hereby incorporated by reference in their entirety.

In one embodiment, cLac is conjugated or linked to a label for imaging purposes. There are a good number of labels known in the art that can be used for imaging in vitro and in vivo. The label can be but not limited to a biotin, a fluorophore, and a radioisotope. Suitable fluorescent dyes for use with cyclic lactadherin mimics described herein include, but are not limited to, Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, Tru-Red (PerCP-Cy5.5 conjugate), Fluor X, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, ALEXA FLUOR 405, ALEXA FLUOR 430, ALEXA FLUOR 488, ALEXA FLUOR 500, ALEXA FLUOR 514, ALEXA FLUOR 532, ALEXA FLUOR 546, ALEXA FLUOR 555, ALEXA FLUOR 568, ALEXA FLUOR 594, ALEXA FLUOR 610, ALEXA FLUOR 633, ALEXA FLUOR 647, ALEXA FLUOR 660, ALEXA FLUOR 680, ALEXA FLUOR 700, ALEXA FLUOR 750, ALEXA FLUOR 790, Cy2, Cy3, Cy3B, Cy3.5, Cy5, Cy5.5, Cy7, nanoparticles, or quantum dots.

Where the label is biotin, standard streptavidin chemistry and colorimetric (chromogen) or fluorescent detection methods can be used. (See INVITROGEN™ Molecular Probes Handbook, Chapter 7, "Avidin and Streptavidin Conjugates-Section 7.6") Commercial biotin-streptavidin detection kits are available, e.g., Biotin-Streptavidin IHC detection kits from ABCAM.

When the label is a fluorophore, standard epifluorescence microscopy and imaging can be used to detect, measure and/or analyze the binding.

When the label is a radioisotope, standard X-ray, CT or PET imaging can be used to detect, measure and/or analyze the binding.

In some embodiments of any one of the cLac described herein, the cyclic lactadherin mimic can be labeled with a radioisotope, including, but not limited to, Iodine 123, Iodine 131, Gallium 67, Indium 111, Fluorine 18, and Technetium 99 m (Tc99m). It will be appreciated by those of skill in the art that Fluorine 18 ($^{18}F$) is a positron emitter, and is thus useful in positron emission tomography (PET). Iodine 123, Iodine 131, Gallium 67, Indium 111, and Technetium 99 m are useful, for example, with standard gamma emission detection.

In one embodiment, the detectable label is a MRI contrast agent. Examples of MRI contrast label include but are not limited to superparamagnetic iron oxide-based contrast label, gadofullerene-based contrast label and nitroxide spin-based contrast label.

In one embodiment, the detectable label is a fluorescent label for near-infrared spectroscopy (NIRS). It is well-established that human tissues are transparent to near-infrared light (650 nm to 1000 nm). Moreover, it has been shown that NIRS can detect intracranial cerebral hematomas through the skin, scalp, and skull in human subjects. NIRS in functional brain studies is a non-invasive tool to monitor local changes in cerebral oxygenation and hemodynamics.

Near-infrared light penetrates through several centimeters of tissue and has been successfully applied to the non-invasive study of skeletal muscle (for muscle perfusion and oxygenation), breast (for tumor detection), and brain (for functional studies) in human subjects.

In some embodiments, the NIRS-sensitive fluorescent chromophore should absorb and emit fluorescence at NIR wavelengths (preferably 700-800 nm) or absorb at NIR wavelengths and have low autofluorescence. There are several commercially available NIR fluorescent chromophores including IRDye® 800CW, IRDye® 680, IRDye® 700DX, Cy5.5, ALEXA® FLUOR 750, ALEXA® FLUOR 680, FluoSpheres Far Red, FluoSpheres Infar red, 1,1'-dioctadecyl-3,3,3',3'-tetramethylinotricarbocyanine iodide (di-R), the various lipophilic indocarbocyanine dyes (DiI, DiA, DiD, DiO, PKH2, PKH26), VIVOTAG-S® 750 and indocyanine green. The indocyanine green is the preferred choice as it is current being used to clinically. Depending on the water solubility of these dyes, the dyes may be mixed with a solvent such as DMSO or packaged in liposomes and introduced by known means such as topically on the skin or intravenously or intrathecally into a subject such as a human.

The NIRS labeled cLac can be detected by a near-infrared tissue spectrometer. Appropriate highpass filters can be incorporated into the photomultiplier to measure the fluorescent signal from these chromophores. The illumination from the NIR laser diode (illumination fiber) will be at a suitable wavelength (which is dependent on the absorption wavelength of the NIR-sensitive chromophore), while the fluorescence emission will be isolated with a long-pass filter at the tip of the detection fiber. Methods of detecting NIRS-sensitive chromophore in vivo are known in the art. For example, described in Park et al., J. 2011, Am. Chem. Soc. 133:2832-2835 and Thapa N. et al., 2008, J. Cell MeI. Med. 12: 1649-1660.

In one embodiment, the cLac is selected from the group consisting of WBipGHIQGGRGGGD (SEQ ID NO: 1), WBipGHIQAGRGGGD (SEQ ID NO: 2), WBipGHIQ-GARGGGD (SEQ ID NO: 3), cLac-A5 or WBipGHIQG-GRGGAD (SEQ ID NO: 4), WBipGHIQGGRGGGGD (SEQ ID NO: 5), WBipGHIQGGRGGGGGD (SEQ ID NO:

6), WBipGHppGQGGRGGGD (SEQ ID NO: 7), WBipGHIQGppGRGGGD (SEQ ID NO: 8), WBipGHIQGRGGGD (SEQ ID NO: 9), WBipGHIQGGGRGGGD (SEQ ID NO: 10), WBipGHIQGppGRGGAD (SEQ ID NO: 11), DWBipGHIQGGRGGGD (SEQ ID NO: 12) or a peptide variant thereof.

Figure 1B:
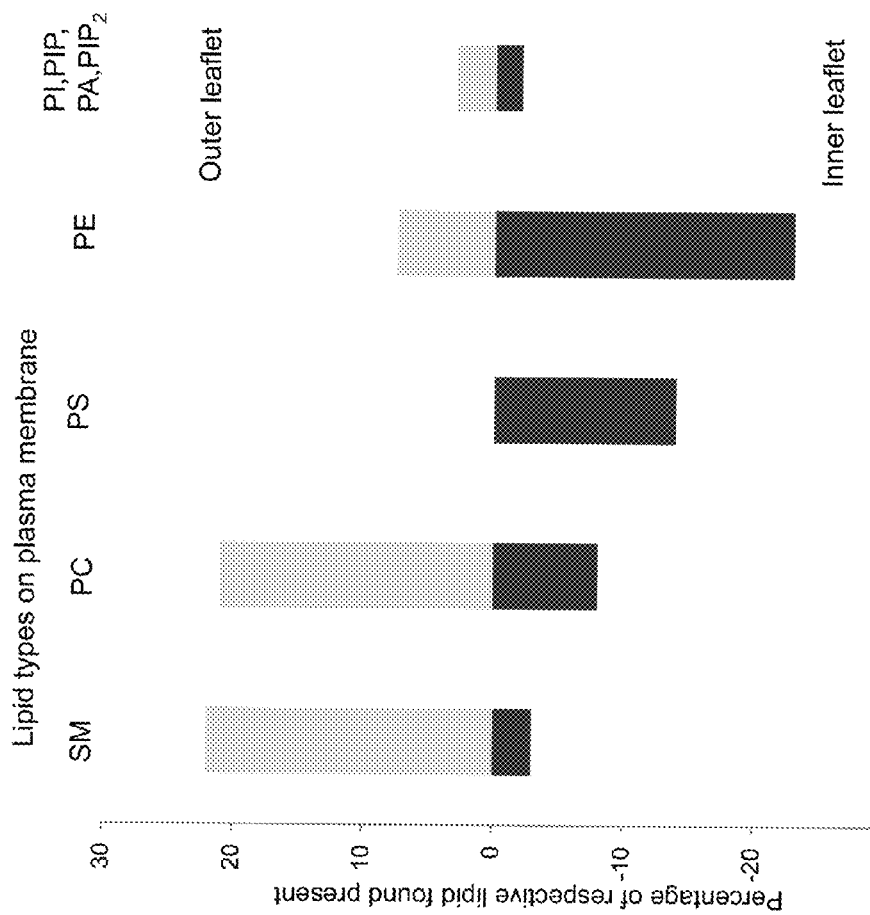
FIG. 1B shows the asymmetric distribution of membrane lipids on the outer leaflet and inner leaflet of a typical bilayer plasma membrane. The y-axis represents the percentage of the respective lipid found present on the inner or outer leaflet of the plasma membrane. The x-axis represents lipid types found in plasma membrane.
Figure 1A:
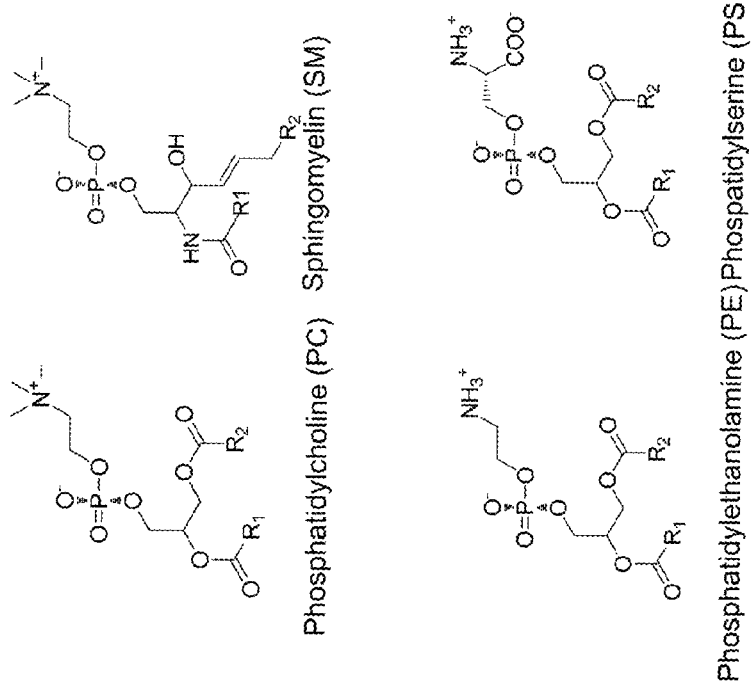
FIG. 1A shows the types of membrane lipids that make up a typical lipid bilayer plasma membrane.

The inventors have shown that the cLac bind specifically to PS. In a living healthy cell, PS is found exclusively on the inner layer of the lipid membrane bilayer (see FIG. 1). However, in certain abnormal cells (e.g., tumor endothelial cells) and dying cells that are either under apoptosis or necrosis have PS exposed on the outer layer of the lipid membrane bilayer. In other words, in these cells, PS is exposed to the cell exterior. It is therefore contemplated that the cLac described herein can be used for detecting these abnormal cells (e.g., tumor endothelial cells) and dying cells undergoing apoptosis or necrosis.

The detection of abnormal cells and dying cells can take place in a laboratory experiment, i.e., the detection is in an in vitro experiment. While not wishing to be bound by theory, these abnormal cells and dying cells have PS exposed on the outer leaflet of the cell's plasma membrane. In this context in a laboratory setting, the cLac are used as research tools, indicator molecules or agents for detecting abnormal and/or dying cells. For example, a new drug is developed to treat cancer and the drug directly or indirectly induced apoptosis in cancer cells found in tumors. To test the effectiveness of the drug in treating different types of cancers, cell lines representing several types of cancers are cultured in vitro and then treated with the drug. After a fixed period of drug treatment, the cells are washed, labeled cLac are added to bind any exposed PS and unbound labeled cLac are washed away. The cell lines that are susceptible to the drug will have increased labeled cLac compared to control cells that are not treated with the drug. Alternatively, biopsy tissues having cancer cells from patients having different types and stages of cancer can be used in the in vitro drug efficacy testing described above.

Accordingly, in one embodiment, provided herein is a composition comprising at least a cLac peptide described herein and a pharmaceutically acceptable carrier. The composition can have more than one cLac peptide described herein and the cLac peptides are different. In one embodiment of any of one of the compositions described herein, the at least one cLac peptide is labeled.

In addition, in one embodiment, provided herein is a kit comprising at least one cLac peptide or a composition described herein and instructions for using the cLac peptide or composition to detecting PS exposure or apoptosis in a biological sample or in a subject. In one embodiment, the kit comprises a cLac that is not labeled with a detectable label. In this embodiment, the kit further comprises at least one detectable label, labeling reagents and labeling instructions. In a further embodiment, the kit further comprises a panel of different detectable label, labeling reagents and labeling instructions for the purpose of allowing the researcher to select and label the cLac according to his experiments.

In another embodiment, the kit comprises a labeled cLac. In another embodiment, the kit comprises more than one type of labeled cLac. For example, the kit comprises three different types of labeled cLac, a Cy5-labeled cLac, a biotin-labeled cLac, and an ALEXA® 488-labeled cLac.

In one embodiment, the kit comprises one variant of cLac, e.g., a cLac comprising SEQ. ID. No. 1. In another embodiment, the kit comprises more than one variant of cLac, e.g., a cLac comprising SEQ. ID. No. 1, a second cLac comprising SEQ. ID. No. 9 and a cLac comprising SEQ. ID. No. 8. In other embodiments, the variants of cLac in the kit can be non-labeled or labeled. In other embodiments, the variants of cLac in the kit can be labeled with different detectable labels.

In one embodiment, provided herein is a kit comprising a composition that comprises at least one cLac described herein, and instructions for using the cyclic peptide to detecting PS exposure or apoptosis in a biological sample or in a subject.

In one embodiment, provided herein is a method of detecting PS exposure on a cell, comprising contacting a biological sample comprising the cell with a cLac or a composition described herein, and measuring or detecting the amount of cLac attached to the biological sample, wherein if the amount of cLac attached is above a control reference level or the detected cLac in biological sample is above that of the background indicates the presence of PS exposure on the cells in the biological sample. In one embodiment, the cLac is non-label or labeled. In one embodiment, the method further comprising a washing step to remove unbound cLac.

In one embodiment, provided herein is a method of detecting apoptosis of a cell or a tissue in a biological sample, comprising contacting the biological sample with a cLac or a composition described herein and measuring the cyclic peptide attached to the biological sample, wherein the amount of cyclic peptide attached is above a control reference level indicates the presence of apoptosis in the biological sample. In another embodiment, when the detected cLac in biological sample is above that of the background indicates the presence of apoptosis in the biological sample. In one embodiment, the cLac is non-label or labeled. In one embodiment, the method further comprising a washing step to remove unbound cLac.

In one embodiment, provided herein is a method of detecting apoptosis in a tissue in a subject in need thereof, the method comprises contacting the tissue with the cLac or a composition described herein and measuring the cyclic peptide attached to the tissue, wherein the amount of cyclic peptide attached is above a control reference level or background indicates the presence of apoptosis in the tissue. In one embodiment, the method further comprises administering to the subject a cLac or a composition described herein to effectuate the contacting. In one embodiment, the method further comprises selecting a subject in need thereof detecting apoptosis in a tissue, e.g., a subject being treated for cancer or an organ transplant subject.

In one embodiment, provided herein is a method for measuring the efficacy of a treatment in a subject in need thereof, the method comprising (i) detecting a level of apoptosis in the subject using any of the methods described herein prior to administering a treatment and (ii) detecting a level of apoptosis in the subject using any of the methods described herein after administering the treatment, wherein a difference in the level of apoptosis in the subject after administering the treatment relative to the level of apoptosis in the subject before administering the treatment is indicative of the treatment being effective. In one embodiment, the level of apoptosis in the subject after administering the treatment is higher than prior treatment when increased apoptosis is desired in the treatment, e.g., in cancer treatment. In another embodiment, the level of apoptosis in the subject after administering the treatment is lower than prior treatment when decreased apoptosis is desired in the treatment, e.g., in an immunosuppressant treatment for an organ transplant subject. In one embodiment, the method further comprises administering to the subject a cLac or a composition described herein. In one embodiment, the method further comprises selecting a subject in need of treatment efficacy evaluation, e.g., a subject being treated for cancer or an organ transplant subject.

It is also contemplated that during a course of treatment, the level of apoptosis in the subject can be monitored over a period of time. In the embodiments where multiple measurements of the level of apoptosis in the subject are taken, it is contemplated that the level of apoptosis in the subject at a later time period during the course of treatment is compared to the level of apoptosis in the same subject an earlier time period during the course of treatment.

In one embodiment, provided herein is a method for measuring the efficacy of a treatment in a patient in need thereof, the method comprising (i) detecting a level of apoptosis in the subject using any of the methods described herein at a first time period after administering a treatment and (ii) detecting a level of apoptosis in the subject using any of the methods described herein at a second time period after administering the treatment, wherein the second time period is later than the first time period, (iii) comparing the levels of (i) with (ii) wherein a difference in the level of apoptosis in the subject the second time period relative to the level of apoptosis to the first time period is indicative of the treatment being effective.

In one embodiment, the treatment's goal is to arrest or reduce apoptosis, e.g., immune suppression for organ transplant rejection. In another embodiment, the treatment's goal is to promote or increase apoptosis, e.g., an anti-cancer treatment.

In some embodiments of the methods of efficacy described herein, when the treatment's goal is to promote or increase apoptosis, the difference of level of apoptosis between the second time point and a first time point is an increase, e.g., in cancer treatment. In other embodiments of the methods described herein, when the treatment's goal is to arrest or reduce apoptosis, the difference of level of apoptosis between the second time point and a first time point is a decrease, e.g., in organ transplant rejection, occlusion vascular disease, or infection. In some embodiments, the increase is at least 5%. In other embodiments, the increase is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% above the level of apoptosis prior to treatment or compared to an earlier time point when the level of apoptosis was assessed. In some embodiments, the decrease is at least 5%. In other embodiments, the decrease is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% below the level of apoptosis prior to treatment or compared to an earlier time point when the level of apoptosis was assessed.

In some embodiments, the methods described herein provide a quick way to determine whether a treatment is working or not at an early phase of the treatment. The method also provides a rapid method of selecting an effective treatment for a subject in need thereof, where there are several treatment options for the subject or the particular ailment or disease. For example, in a typical breast cancer treatment, the subject may be treated with e.g., chemotherapy (CMF: cyclophosphamide, methotrexate, and fluorouracil) and/or irradiation therapy, for a period of one or two months after which the treatment efficacy is assessed. Methods of assessing cancer treatment efficacy are well known in the art to a skilled clinician, physician or oncologist. For example, assessing the shrinkage in size and reduction in the number of tumors by imaging by computed tomography (CT) scans, magnetic resonance imaging (MRI), positron emission tomography (PET), and ultrasound scans, measurement of the level of biomarkers that are known to be associated with the type of cancer (e.g., urinary N-terminal cross-linked type 1 collagen telopeptide (uNTx), C-terminal cross-linked type 1 collagen telopeptide (CTX), Alpha-fetoprotein (AFP), beta-human chorionic gonadotropin ($\beta$-HCG), beta2 ($\beta$2)-microglobulin), calcitonin, carbohydrate antigen 125 (CA-125), carbohydrate antigen 19-9 (CA 19-9), Carbohydrate antigen 27.29 (CA27.29), rcinoembryonic antigen (CEA), lactate dehydrogenase, prostate-specific antigen (PSA), and thyroglobulin), quantitative measurement of metabolically active tumor by determining the metabolic unit volume (MUV) by FDG PET/CT imagery (Jethya C, et al., J Nucl Med. 2008; 49 (Supplement 1):121P), laser-correlation spectrometry (LCS) of blood plasma and serum for malignant neoplasms (Akleyev et al., Proc. SPIE, 5973:597302 (2005)), and assessing skeletal-related event (SRE), pain scores, analgesic consumption, and quality of life (QoL) scores (Clemons M., et al., The Oncologist 2006 11: 227-233). Instead of waiting for one or two months for the chemotherapy or radiation to shrink the tumors and/or reduce the level of circulating cancer biomarkers, the methods described herein can be used within the first few doses of chemotherapy or radiation, within the period of less than a week and anytime up to two weeks after the start of treatment. The methods allow the clinician to quickly determine if the specific chemotherapy or radiation is effective in inducing apoptosis of the cancer cells by way of detecting an increase in the level of apoptosis using the labeled cLac or variants described herein. If the first few cancer treatment doses resulted in no detectable increase in apoptosis at the tumor site(s), this indicates that that specific treatment protocol is not working. The clinician can then change to another treatment protocol. For example, change the CMF chemotherapy to GET: gemcitabine, epirubicin, and taxol regimen. Early evaluation of treatment efficacy allows the clinician on try several treatments options and select an effective one within a relatively short period of time after the initial diagnosis and/or staging of cancer, before the cancer has spread extensively and progress to a late stage cancer. Early identification of an effective treatment protocol reduces the time and opportunities for the cancer spread extensively and progress to a late stage cancer and this provides better treatment prognosis for the subject.

The term "effective" when used with respect to a medical ailment or disease treatment protocol refers to the treatment protocol that produces at least 5% increase or decrease in the level of apoptosis and/or PS detected in the tissue being treated in subject. The level of apoptosis and/or PS can be detected and analyzed by any methods known in the art, includes the methods described herein.

Accordingly, in one embodiment, provide herein is a rapid method of selecting an effective treatment for a subject in need thereof, the method comprises of detecting a level of apoptosis in a tissue in a subject after the start of a treatment and comparing the detected level of apoptosis to a control reference or background reference wherein if the detected level of apoptosis is above a control reference or background indicates that the treatment is effective and the treatment should be continued, and wherein if the detected level of apoptosis is below or no different than the control reference or background indicates that the treatment is not effective and the treatment should be discontinued.

In one embodiment, the subject is diagnosed with a medical ailment or disease wherein cell death, apoptosis or necrosis is one desired effect of the treatment of the medical ailment or disease, e.g., cancer.

In one embodiment of the method, the method further comprises selecting a subject who is diagnosed with a medical ailment or disease wherein cell death, apoptosis or necrosis is one desired effect of the treatment of the medical ailment or disease.

In one embodiment, the subject is diagnosed with a medical ailment or disease wherein cell death, apoptosis or necrosis is a consequential effect of the ailment or disease, e.g., autoimmune disease, organ transplant rejection etc.

Accordingly, in this embodiment, provide herein is a rapid method of selecting an effective treatment for a subject in need thereof, the method comprises of detecting a level of apoptosis in a tissue in a subject after the start of treatment and comparing the detected level of apoptosis to a control reference or background reference wherein if the detected level of apoptosis is above a control reference or background indicates that the treatment is ineffective and the treatment should not be continued, and wherein if the detected level of apoptosis is below or no different than the control reference or background indicates that the treatment is effective and the treatment should be continued, wherein the treatment is for a medical ailment or disease wherein cell death, apoptosis or necrosis is a consequential effect of the ailment or disease. In one embodiment of this method, the method further comprises selecting a subject who is diagnosed with a medical ailment or disease wherein cell death, apoptosis or necrosis is a consequential effect of the ailment or disease.

In one embodiment, the level of apoptosis in a tissue in the subject is analyzed shortly after the start of treatment. In one embodiment, the level of apoptosis in a tissue in the subject is analyzed within the period of less than a week and anytime up to two weeks after the start of treatment. In some embodiments, the analysis is performed on the first, second, third, fourth, five, sixth, seventh, eighth, ninth, tenth, eleventh, twelfth, thirteenth or fourteenth day after the start of treatment.

In one embodiment, the level of apoptosis is detected in vitro. A biological sample of the tissue is extracted from in the subject. In one embodiment, the biopsy tissue sample is sent to a laboratory for analysis. In one embodiment, the biopsy tissue sample is analyzed at where the biopsy extraction occurred, e.g., the doctor's office or surgical procedure room. The use of a commercial apoptosis/PS detection kit will be convenient for this purpose. As such, in one embodiment, the biological sample is contacted with a cLac or a composition comprising cLac described herein, and sufficient time is allowed for binding of the cLac to the exposed PS on the apoptotic cells of the tissue. Excess unbound cLac is then washed off.

In one embodiment, the biological sample is fixed before analysis, i.e., contacting with cLac or with a composition described herein. In one embodiment, the biological sample is fixed as soon as it was extracted from the subject. In one embodiment, the biological sample is fixed within one hour of extraction. In one embodiment, the biological sample is fixed no more than five hour of extraction. One can use any method known in the art that does not affect the PS exposed in the cell surface. Methods of fixing tissue samples are well known in the art, e.g., with paraformaldehyde.

In one embodiment, the biological sample is analyzed as soon as it was extracted from the subject. In one embodiment, the biological sample is analyzed within one hour of extraction. In one embodiment, the biological sample is analyzed no more than five hour of extraction.

In one embodiment, the level of apoptosis is detected in vivo. The tissue in the subject that is to be analyzed is contacted with a cLac in vivo. In one embodiment, the contacting is by way of administering the cLac or a composition comprising cLac described herein to the subject. In one embodiment, if the tissue is accessible by direct injection, e.g., breast and skin cancer, the cLac or composition described herein is injected directly to the tissue. In one embodiment, if the tissue is not easily accessible by direct injection, a catheter can used to deliver the cLac or composition to the tissue, e.g., the heart, or the cLac or composition described herein can be delivered by intravenous injection, to the blood vessel/artery as close to the tissue or supplying the tissue, e.g., hepatic artery for liver cancer or carotid artery for brain tumor.

In one embodiment, the level of apoptosis is detected in vivo by measuring the detectable signal from the labeled cLac. Depending on the type of label on the cLac, a skilled clinician will be able to select an appropriate detection or measuring method for the specific detectable signal emitted by the labeled cLac. Accordingly, in some embodiments, the detectable signal from the labeled cLac is detected or measured by any methods known in the art. In one embodiment, the detectable signal from the labeled cLac is detected by MRI, CT, NIR or PET scans.

In one embodiment, the detection of PS exposure or apoptosis can be in vitro, ex vivo or in vivo.

In one embodiment, the biological sample can be from any tissue from a subject. For example, from the lungs, kidney, brain, skin, liver, bladder, pancreas, skeletal muscles, bone, intestines, stomach and heart. In one embodiment, the biological sample from a subject afflicted with an ailment or disease. In one embodiment, the ailment or disease is cancer or a malignant condition, vascular occlusive disease, myocardial infarction, kidney failure, hepatitis or bacterial infection.

In one embodiment of the described methods, the control reference level is the amount of cLac bound to a biological sample comprising health cells not undergoing apoptosis or necrosis. In another embodiment, the control reference is the average amount of cLac attached to healthy biological samples or tissues not undergoing apoptosis. The biological samples or tissues can be those obtained for a control population of healthy patients.

In another embodiment, the healthy biological samples or tissues can be those from or obtained from a control population of patients having an ailment or disease, e.g., cancer. In yet another embodiment, the healthy biological samples or tissues can be those from or obtained from a control population of patients having an ailment or disease and have not been treated with a drug that promotes apoptosis.

In one embodiment, the number of patients in the control population can range from 5-2000. In one embodiment, the subjects in the control population also have the same stage of cancer of ailment as the subject from which the tested biological sample was obtained, i.e. they are cancer stage-matched with the subject. In one embodiment, the subjects in the control population are also aged-matched within an age range. In one embodiment, the subjects in the control population are gender-matched. In one embodiment, the patients in the control population are also race-matched, e.g., Caucasians, African, Hispanic, Asian etc.

In another embodiment, the control reference level is the detection signal obtained in a biological sample in the absence of cLac, i.e., the background signal. The biological sample of the reference is the same as that used for detecting PS exposure on a cell or a tissue.

In one embodiment, the background is the level of cLac detected in a biological sample or tissue when cLac has not provided for contacting with the biological sample. In other words, cLac was omitted in the detection method as a control.

In another embodiment, the background is the level of cLac detected in a biological sample or tissue when non-labeled cLac was used in contacting with the biological sample or tissues.

In one embodiment, when the amount of cyclic peptide attached to the biological sample is at least 10% above the control reference or the background indicates the presence of phosphatidylserine exposure on the cells in the biological sample.

In one embodiment, when the amount of cyclic peptide attached to the biological sample or tissue is at least 10% is above the control reference or the background indicates the presence of apoptosis in the biological sample or in the tissue of the subject.

In some embodiments, the amount of cyclic peptide attached to the biological sample or tissue is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% above the control reference or the background indicates phosphatidylserine exposure on the cells and/or the presence of apoptosis in the biological sample or tissue in the subject.

In one embodiment of the methods described, the cLac is labeled with a fluorescent label, a colorometric dye, a magnetic resonance imaging contrast label, a radioisotope, a biotin or a positron emission tomography imaging label.

In some embodiments of methods described, depending on the detectable label on the cLac, the labeled cLac can be detected by the label's electromagnetic emission, by colorimetric methods, by radiation emitted and by positron particle emitted.

In one embodiment of the methods described, the subject has a cancer or malignant condition, vascular occlusive disease or myocardial infarction. Vascular occlusive disease aka peripheral vascular disease includes a group of diseases in which blood vessels become restricted or blocked. Typically, the patient has peripheral vascular disease from atherosclerosis. Atherosclerosis is a disease in which fatty plaques form in the inside walls of blood vessels. Other processes, such as blood clots, further restrict blood flow in the blood vessels. Both veins and arteries may be affected, but the disease is usually arterial. All the symptoms and consequences of peripheral vascular disease are related to restricted blood flow. Peripheral vascular disease is a progressive disease that can lead to necrosis and gangrene of the affected area. Peripheral vascular disease may also occur suddenly if an embolism occurs or when a blot clot rapidly develops in a blood vessel already restricted by an atherosclerotic plaque, and the blood flow is quickly cut off.

In one embodiment of the method described, the method further comprises selecting a subject who has been diagnosed with cancer, a vascular occlusive disease or myocardial infarction.

In one embodiment, as used herein, "cancer" refers to any of various malignant neoplasms characterized by the proliferation of anaplastic cells that tend to invade surrounding tissue and metastasize to new body sites and also refers to the pathological condition characterized by such malignant neoplastic growths.

In one embodiment of the methods described, the subject is diagnosed with cancer. Methods of diagnosing cancer are known to a skilled physician. In general, cancer is suspected based on a person's symptoms, the results of a physical examination, and the results of screening tests such as imaging. Imaging tests often include plain x-rays, ultrasonography, CT, and MRI. These tests assist in identifying abnormalities, determining qualities of a mass (solid or cystic), providing dimensions, and establishing relationship to surrounding structures, which can be important if surgery or biopsy is being considered. Occasionally, x-rays obtained for other reasons such as an injury, show abnormalities that might be cancer. Confirmation that cancer is present requires other tests (termed diagnostic tests e.g, by tumor biopsy and histopathologic examination). Other screening tests include but are not limited to screening the level of serum tumor markers the findings of which are suggestive of a specific cancer. For examples α-Fetoprotein (hepatocellular carcinoma, testicular carcinoma), carcinoembryonic antigen (colon cancer), β-human chorionic gonadotropin (choriocarcinoma, testicular carcinoma), serum immunoglobulins (multiple myeloma), DNA probes (e.g., bcr probe to identify a chromosome 22 alteration in chronic myelogenous leukemia), CA 125 (ovarian cancer), CA 27-29 (breast cancer), prostate-specific antigen (prostate cancer).

After cancer is diagnosed, it is staged. Staging is a way of describing how extensive or advanced the cancer is in terms of its location, size, growth into nearby structures, and spread to other parts of the body. People with cancer sometimes become impatient and anxious during staging tests, wishing for a prompt start of treatment. However, staging allows doctors to determine the most appropriate treatment as well as helping to determine prognosis.

Staging may use scans or other imaging tests, such as x-ray, CT, MRI, bone scintigraphy, or positron emission tomography (PET). The choice of staging test(s) depends on the type of cancer, as different cancers involve different parts of the body. CT scanning is used to detect cancer in many parts of the body, including the brain and lungs and parts of the abdomen, including the adrenal glands, lymph nodes, liver, and spleen. MRI is of particular value in detecting cancers of the brain, bone, and spinal cord.

Biopsies are often needed for staging and can sometimes be done together with the initial surgical treatment of a cancer. For example, during a laparotomy (an abdominal operation) to remove colon cancer, a surgeon removes nearby lymph nodes to check for spread of the cancer. During surgery for breast cancer, the surgeon biopsies or removes lymph nodes located in the armpit to determine whether the breast cancer has spread there; this information along with features of the primary tumor helps the doctor determine whether further treatment is needed. When staging is based only on initial biopsy results, physical examination, and imaging, the stage is referred to as clinical. When the doctor uses results of a surgical procedure or additional biopsies, the stage is referred to as pathologic. The clinical and pathologic stage may differ.

In addition to imaging tests, doctors often obtain blood tests to see if the cancer has begun to affect the liver, bone, or kidneys.

In one embodiment of the methods described, the cancer for the methods described herein include but are not limited to carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include but are not limited to papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include but are not limited to, for example, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

In one embodiment of the methods described, the subject having the cancer or malignant condition is undergoing a cancer therapy. In some embodiments, the cancer therapy is chemotherapy, radiation therapy, immunotherapy or combination thereof.

In one embodiment of the methods described, the subject is an organ transplant recipient and is undergoing immunosuppression therapy. In one embodiment, the immunosuppression therapy is long-term. In another embodiment, the subject is a second time organ transplant recipient and is undergoing immunosuppression therapy, i.e., one whose body had previously rejected the first or even the second donor organ.

In one embodiment, the contacting of tissue is by way of administering the cLac into the subject, e.g., by injecting intravenously or direct injection into the tumor or affected tissue.

In one embodiment of the method described, the cLac is formulated to be delivered with or in a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition comprising the cLac described herein is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

In one embodiment, the cLac formulation or composition described herein is not immunogenic when administered to a subject. In one embodiment, as used herein, the terms "pharmaceutically acceptable" and grammatical variations thereof, as they refer to compositions, carriers, diluents and reagents, are used interchangeably and represent that the materials are capable of administration to or upon a subject without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The cLac formulation or compositions for the methods described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

The method of delivering the cLac formulation or compositions described herein will vary based on the individual subject, the type and location of cancer, or ailment or diseases and other criteria evident to one of ordinary skill in the art. Delivery methods include direct injection at the disease/cancer/tumor site, percutaneous delivery for injection, percutaneous delivery for topical application, and other delivery methods well known to persons of ordinary skill in the art.

Routes of administration include, but are not limited to, topical, transdermal, direct injection, intradermal, intramuscular, intraperitoneal, intravenous, subcutaneous, intranasal, epidural, and oral routes. Administration can be systemic or local.

The present invention can be defined in any of the following numbered paragraphs:

[01] A cyclic peptide comprising at least 10 but no more than 20 amino acid residues having the formula I:

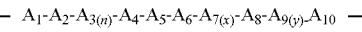

$A_1$-$A_2$-$A_{3(n)}$-$A_4$-$A_5$-$A_6$-$A_{7(x)}$-$A_8$-$A_{9(y)}$-$A_{10}$ wherein $A_1$ and $A_2$ are hydrophobic amino acid residues that are appropriate for lipid membrane binding, wherein the side chains of these hydrophobic amino acid have an added cLogP value of between 5 and 9, and wherein the hydrophobic amino acid residues are in the D or L configuration, are natural or unnatural, and hydrophobic amino acid are substituted or unsubstituted;

wherein $A_4$ is an amino acid with polar side chain that can form strong hydrogen bonding or salt bridge;

wherein $A_5$ is a small hydrophobic amino acid;

wherein $A_6$ is an amino acid with polar side chain that can form strong hydrogen bonding;

wherein $A_3$, $A_7$ and $A_9$ are neutral amino acid residues, wherein n=1-3, x=1-5 and y=2-6, and when there are multiples of $A_3$, $A_7$ and $A_9$, they can be the same amino acid residues or different amino acid residues;

wherein $A_8$ is a positively charged amino acid; and wherein $A_{10}$ is an amino acid with a negatively charged side chain.

[02] The cyclic peptide of paragraph 1, wherein the substituent is a halogenated aromatic or aliphatic amino acid, a halogenated aliphatic or aromatic modification on the hydrophobic side chain, or an aliphatic or aromatic modification.

[03] The cyclic peptide of paragraph 2, wherein the aliphatic modification is between 1 to 10 carbons, and wherein the aliphatic modification is straight chain alkyl or alkenyl.

[04] The cyclic peptide of any one of paragraphs 1-3, wherein $A_1$ and $A_2$ are each individually selected from the group consisting of alanine, glycine, histidine, proline, serine, threonine, tyrosine, cysteine, methionine, valine, tryptophan, phenylalanine, leucine, isoleucine, biphenylalanine, methyl-phenylalanine, terphenylalnine, p-phenyl-L-phenylalanine, 3-(2-naphthyl)-L-alanine, 3-(1-naphthyl)-L-alanine, 4-Iodo-L-phenylalanine, 4-tert-bultyl-L-phenylalanine, 4-Bromo-L-phenylalanine, 3,4,5-Trifluoro-L-phenylalanine, and pentafluoro-L-phenylalanine.

[05] The cyclic peptide of any one of paragraphs 1-4, wherein $A_4$ is selected from the group consisting of histidine, asparagine, glutamine, lysine, arginine and its analogues and derivatives.

[06] The cyclic peptide of any one of paragraphs 1-5, wherein $A_5$ is selected from the group consisting of isoleucine, alanine, valine, leucine and methionine.

[07] The cyclic peptide of any one of paragraphs 1-6, wherein $A_6$ is selected from the group consisting of glutamine, tyrosine, serine, asparagine, histidine, cysteine and threonine.

[08] The cyclic peptide of any one of paragraphs 1-7, wherein $A_3$, $A_7$ and $A_9$ are each individually selected from the group consisting of glycine, alanine, valine, leucine, isoleucine, cysteine, tyrosine, tryptophan, serine, threonine, proline, methionine, phenylalanine, glutamine, asparagine and propargyl glycine (ppG).

[09] The cyclic peptide of any one of paragraphs 1-8, wherein $A_3$, $A_7$ and $A_9$ are each individually alanine or glycine.

[10] The cyclic peptide of any one of paragraphs 1-8, wherein $A_8$ is selected from the group consisting of lysine, arginine and the analogues and derivatives of these amino acids.

[11] The cyclic peptide of any one of paragraphs 1-9, wherein $A_{10}$ is selected from the group consisting of aspartic acid, glutamic acid and the analogues and derivatives of these amino acids.

[12] The cyclic peptide of any one of paragraphs 1-10, wherein the cyclic peptide binds to phosphatidylserine.

[13] The cyclic peptide of any one of paragraphs 1-12 further comprising a linker molecule.

[14] The cyclic peptide of any one of paragraphs 1-13, wherein the cyclic peptide is selected from the group consisting of WBipGHIQGGRGGGD (SEQ ID NO: 1), WBipGHIQAGRGGGD (SEQ ID NO: 2), WBipGHIQGARGGGD (SEQ ID NO: 3), cLac-A5 or WBipGHIQGGRGGAD (SEQ ID NO: 4), WBipGHIQGGRGGGD (SEQ ID NO: 5), WBipGHIQGGRGGGGGD (SEQ ID NO: 6), WBipGHppGQGGRGGGD (SEQ ID NO: 7), WBipGHIQGppGRGGGD (SEQ ID NO: 8), WBipGHIQGRGGGD (SEQ ID NO: 9), WBipGHIQGGGRGGGD (SEQ ID NO: 10), WBipGHIQGppGRGGAD (SEQ ID NO: 11), D-WBipGHIQGGRGGGD (SEQ ID NO: 12) or a peptide variant thereof.

[15] The cyclic peptide of any one of paragraphs 1-14, further comprising a label.

[16] The cyclic peptide of paragraph 15, wherein the label is a fluorescent label, a magnetic resonance imaging contrast label or positron emission tomography imaging label.

[17] A composition comprising a cyclic peptide of any one of paragraphs 1-16 and a pharmaceutically acceptable carrier.

[18] A kit comprising a cyclic peptide of any one of paragraphs 1-16 or a composition of paragraph 17, and instructions for using the cyclic peptide or composition to detect phosphatidylserine exposure or apoptosis in a sample.

[19] A method of detecting phosphatidylserine exposure on a cell, comprising contacting a biological sample with the cyclic peptide of any one of paragraphs 1-16 or with a composition of paragraph 17 and measuring the cyclic peptide attached to the biological sample, wherein the amount of cyclic peptide attached is above a reference level indicates the presence of phosphatidylserine exposure on a cell in the biological sample.

[20] A method of detecting apoptosis of a cell, comprising contacting a biological sample with the cyclic peptide of any one of paragraphs 1-16 or with a composition of paragraph 17 and measuring the cyclic peptide attached to the biological sample, wherein the amount of cyclic peptide attached is above a reference level indicates the presence of apoptosis in the biological sample.

[21] A method of detecting apoptosis in a tissue in a subject in need thereof, contacting the tissue with the cyclic peptide of any one of paragraphs 1-16 or with a composition of paragraph 17 and measuring the cyclic peptide attached to the tissue, wherein the amount of cyclic peptide attached is above a reference level indicates the presence of apoptosis in the tissue.

[22] The methods of paragraphs 19, 20, or 21, wherein the cyclic peptide is labeled with a fluorescent label, a magnetic resonance imaging contrast label or positron emission tomography imaging label.

[23] The method of paragraph 21 or 22, wherein the subject has a cancer or malignant condition, vascular occlusive disease or myocardial infarction.

[24] The method of paragraph 23, wherein the subject having the cancer or malignant condition is undergoing a cancer therapy.

[25] The method of paragraph 21 or 22, wherein the subject is an organ transplant recipient.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLES

Design and Testing of Cyclic Lactadherin Peptide Mimetic (cLac)

Figure 2:
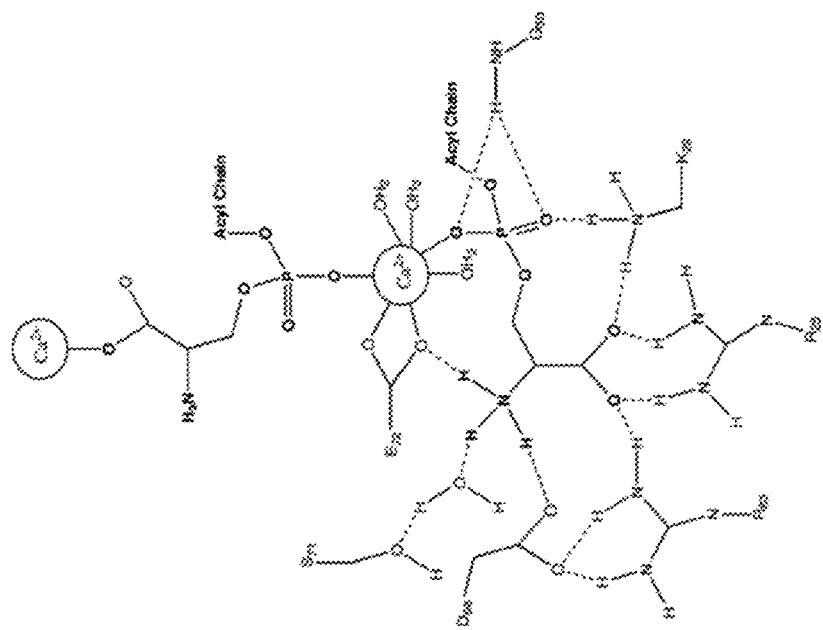
FIG. 2 depicts annexin V and mimetics for phosphatidylserine (PS) binding according to Lemmon, M. A., Nat. Rev. Mol. Cell. Biol. 2008, 9:99 and Smith, B. D., Bioorg. Med. Chem., 2005, 13:5035.
Figure 2:
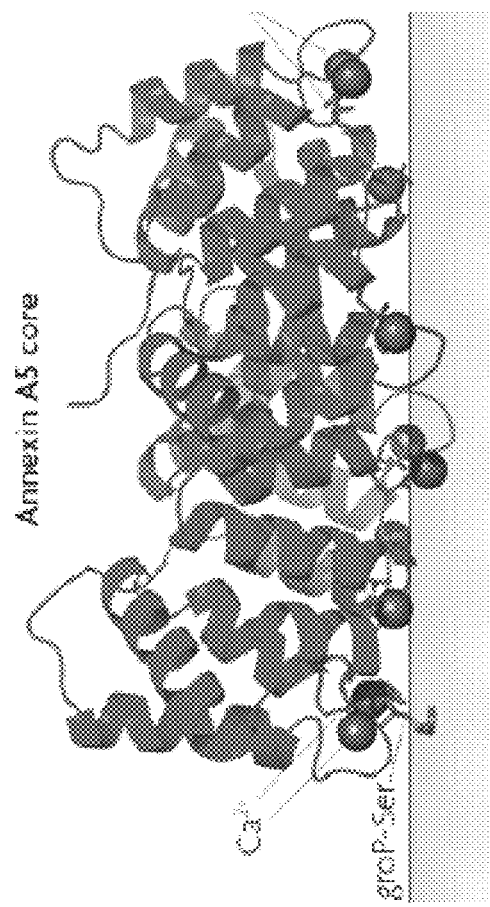
Figure 2:
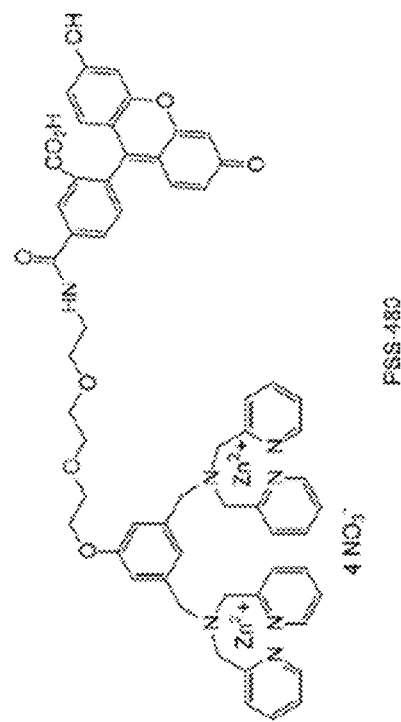

The composition and dynamic distribution of lipid molecules on a biological membrane have been shown to play a critical role in numerous cellular events. For example, the lipid phosphatidylserine (PS) is exclusively localized in the inner leaflet of the membrane in healthy cells (see FIG. 1). The translocation of PS to the outer leaflet is an indicator that a cell is going through apoptosis. Recently, surface presentation of PS has also been reported by endothelial cells of tumor vasculature. Several protein (Annexin V, FIG. 2) and small molecule based probes have been developed to specifically target PS. However, most of them require metal cations (e.g. $Ca^{2+}$ or $Zn^{2+}$) as co-factors and bind PS through electrostatic forces. Therefore, it is the objective of this project to provide are a class of cyclic peptide scaffolds (cLacs) that specifically recognize PS without metal cofactors. Theses cyclic peptides are designed to mimic the naturally-existing PS binding protein, lactadherin (see FIG. 3). The characterization and optimization of this unique PS binding ligand is presented. As described herein, fluorophore-decorated versions or variants of cLac were also synthesized and these cLac peptide variants demonstrate their utility in imaging apoptotic cells.

Lactadherin, also known as milk fat globule-EGF factor 8 (MFG-E8), is a 47 kDa glycoprotein originally found in the milk secreted by mammary epithelial cells. One of its key functions of lactadherin is to mediate the phagocytosis of apoptotic cells by recognizing surface-exposed PS. Lactadherin stereoselectively binds to PS with a nanomolar affinity and without the need of cofactors (FIG. 3).

The major PS binding function of lactadherin has been localized to its C2 domain, which shares homology with the C2 domains of blood coagulation factor VIII and factor V. The crystal structure of the lactadherin C2 domain (Lact-C2) displays a beta-barrel core and three loops projecting out for membrane insertion. While the structure for Lact-C2 bound with PS remains elusive, mutagenesis data as well as computational modeling indicate two potential binding sites (surfaces C and D, as named by Shao et al., 2008, J. Biol. Chem., 283: 7230-7241) for the PS head group. The surface D, in part because computational docking experiments gave a more favorable binding free energy for the PS headgroup than PC (FIG. 4). Further structure analysis revealed a number of residues critical for PS binding (FIGS. 4 and 5). Phe 81 and Trp 26 belong to the group of hydrophobics that insert into the lipid bilayer plasma membranes of cells. The hydrophilic residues (Asp80, His83, Gln95 and Arg148) engage in specific polar interactions with the PS head group that afford the lipid selectivity (FIG. 5). Based on this, it seemed that the PS binding pocket resembles a bowl with the key residues displayed on the rim. The inventors hypothesized, without wishing to be bound or limited by theory, that the circular arrangement of these key residues can be recreated by the scaffold of a cyclic lactadherin peptide mimetic, as described herein.

The first design of a cyclic lac peptide mimetic (cLac-1, FIG. 5) has a Trp and a Phe amino acid residue positioned next to each other to construct a membrane insertion motif (hydrophobic motif). The cLac-1 is also referred to as Lac-Phe. Most of the polar residues (Asp80, His83, and Gln85) involved in PS binding are close in the Lact-C2's primary sequence (see FIGS. 4 and 5). One exception is Arg148, which projects back into the vicinity of the other key residues in the folded protein. For the design of cLac-1, Arg148 was linked to the rest of the cyclic peptide molecule by using two spacers: a dipeptide (-Gly-Gly-, linker I) bridges Gln85 and Arg148, and a tripeptide (-Gly-Gly-Gly-, linker II) links Arg148 and Trp26. Molecular modeling of cLac-1 shows that the two linkers are both long enough and flexible enough to allow a native-like spatial arrangement of these residues for PS complexation.

The cyclic peptide was synthesized using FMOC chemistry. The main chain protected (with allyl) Asp was attached to Wang resin through its side chain. Standard solid phase peptide synthesis afforded the linear precursor with a deprotected N-terminus. Cyclization was accomplished on the resin with HBTU-mediated amide bond formation after removal of the allyl protecting group on Asp.

The peptide-membrane binding was evaluated via a fluorescence assay: large unilamellar vesicles (100 nm in diameter) were prepared with PC and varied percentages of PS. All vesicles contained 5% dansyl-labeled PE to serve as a reporting group. The peptide-vesicle binding was monitored by the fluorescence resonance energy transfer (FRET) from Trp to the dansyl group.

In the starting design, the cLac-1 displayed no binding to lipid vesicles regardless of lipid composition. Presumably, without wishing to be bound or limited by theory, the peptide is too hydrophilic to partition into the membranes. Additional hydrophobic residues (Leu28 and Phe31) are necessary for Lact-C2 to insert into membranes.

Figure 6B:
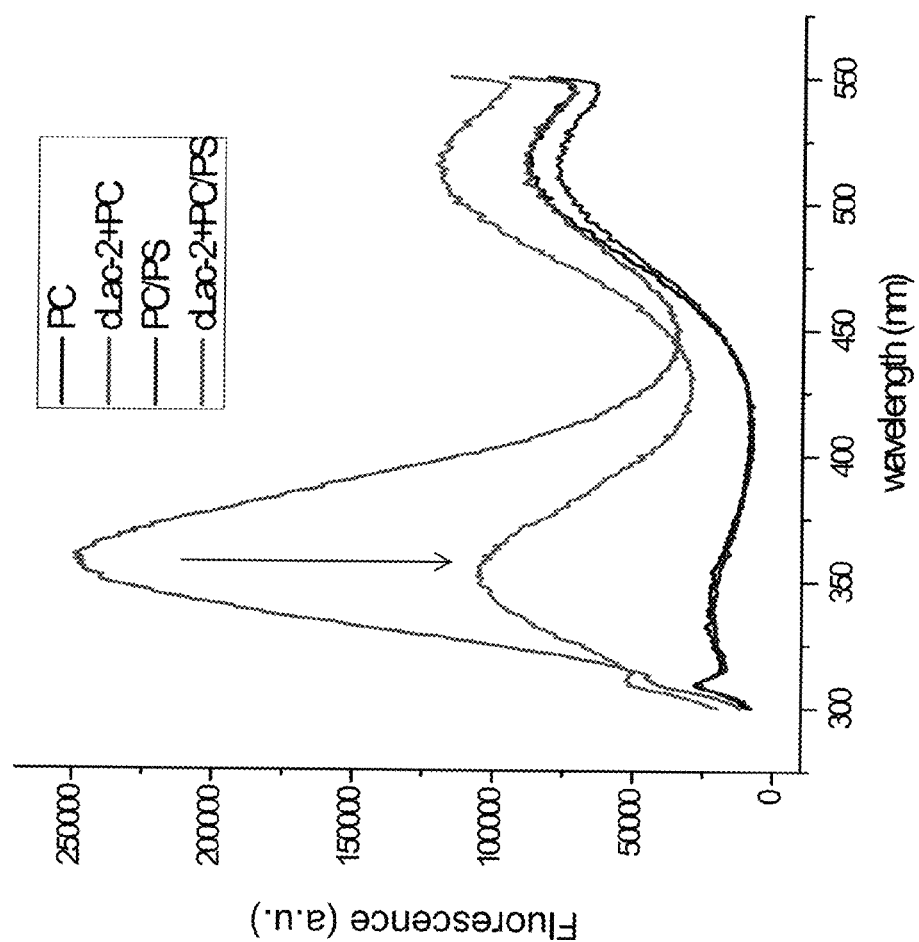
FIG. 6B demonstrates that cLac-2 sensitizes dansyl emission (highlighted by the arrows) only with PC/PS liposomes.
Figure 6A:
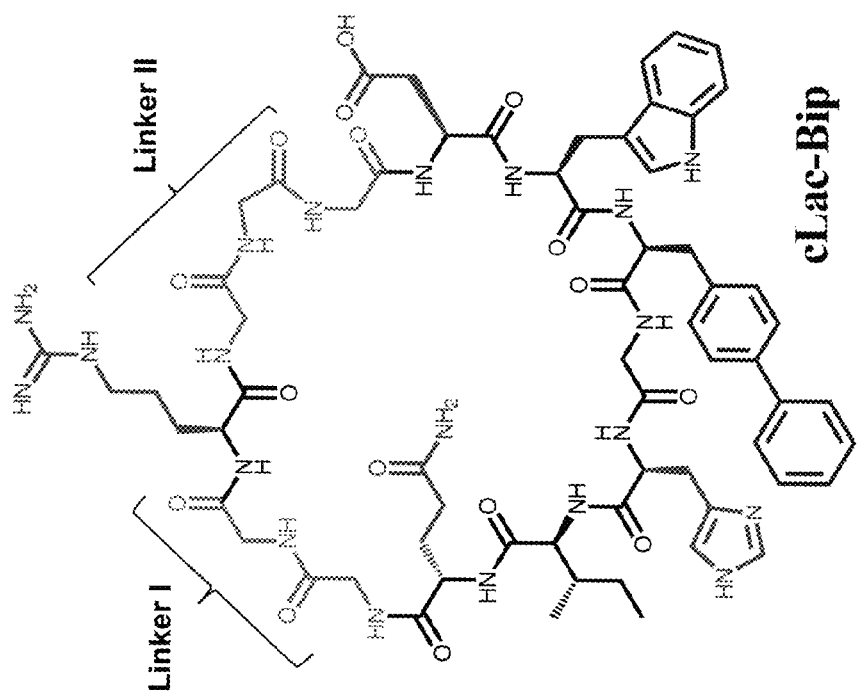
FIG. 6A shows a structure of a more hydrophobic cyclic peptide cLac-Bip, also known as Lac-Bip, cLac-2 and cLac-23G.
Figure 6C:
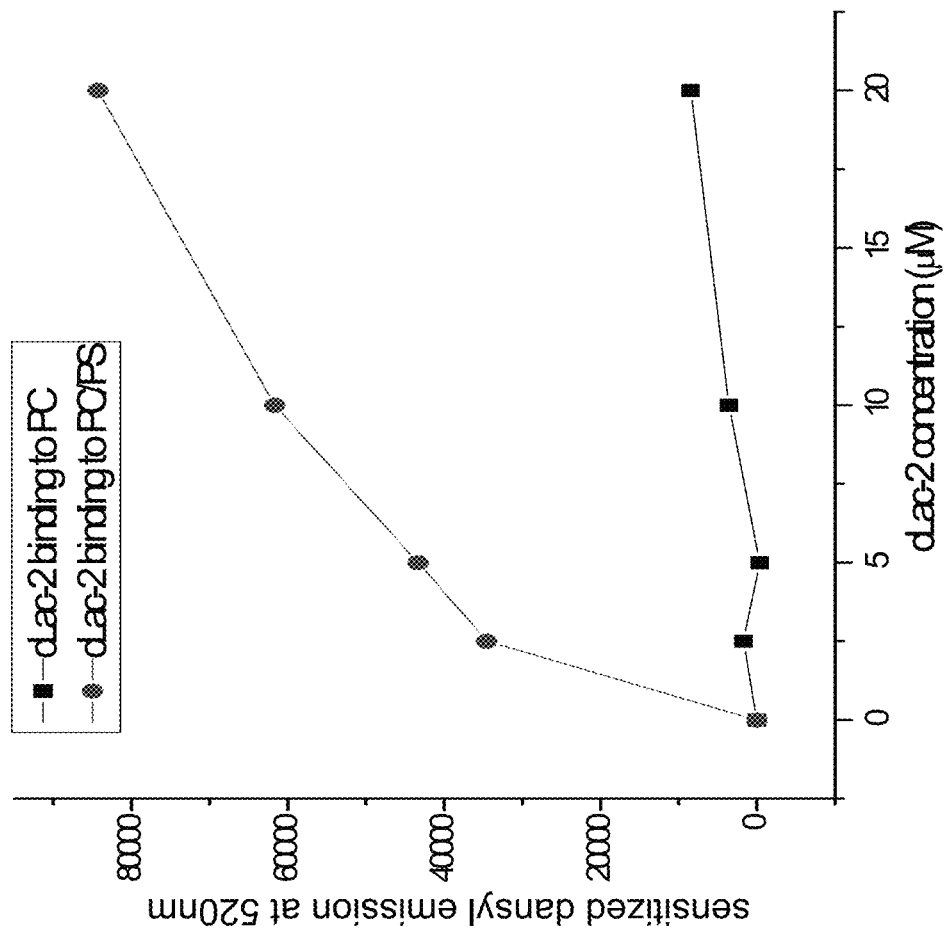
FIG. 6C shows the specificity of binding of cLac-2 to PC/PS liposomes and not PC liposomes.
Figure 6D:
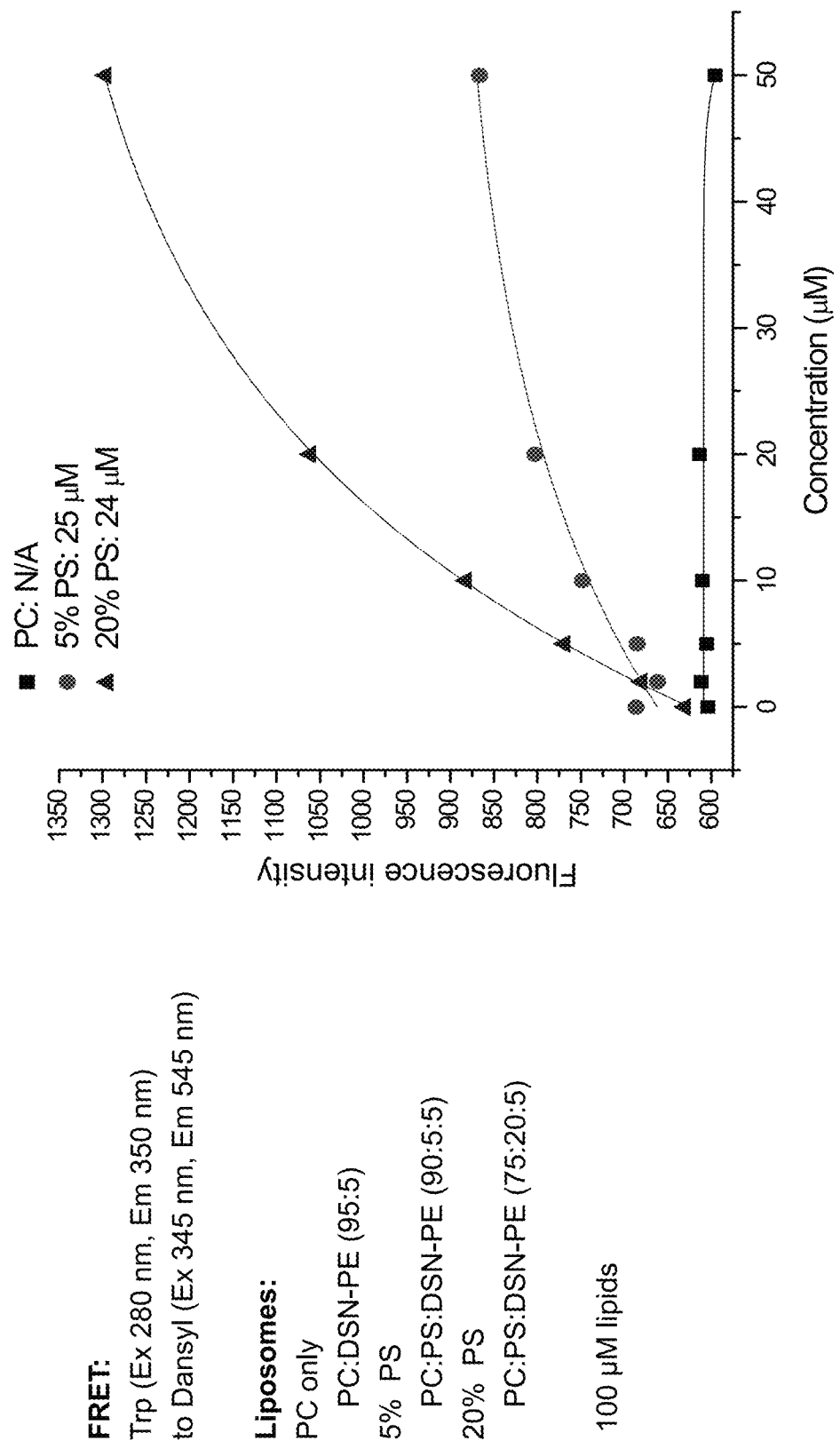
FIG. 6D shows the concentration profiles of cLac-2 binding to membranes with varied PS-containing liposomes.

A more hydrophobic analogue cLac-2 (FIG. 6A) was synthesized, which incorporates a biphenylalanine (Bip) to replace the Phe residue. The cLac-2 is also labeled elsewhere cLac-23G, Lac-Bip, or cLac-Bip. The side chain of Bip has a cLogP value of 4.5, much greater than that of Phe (cLogP: 2.6). The FRET experiment shows no binding of cLac-2 to the PC-alone liposomes (FIGS. 6B and 6C). However, mixing cLac-2 with the PC/PS vesicles clearly elicits a sensitized dansyl emission at 520 nm with a concurrent decrease of Trp emission near 350 nm (FIGS. 6B and 6C). Furthermore, the sensitized dansyl emission becomes stronger with increasing concentrations of cLac-2 (FIG. 6C). The titration results display a saturation profile, yielding an apparent dissociation constant (Kd) of ~15 μM. With cLac-2 at the saturating concentration (50 μM), the sensitized dansyl emission displays a linear dependence on the amount of PS presented by the membranes: vesicles containing 20% PS give close to fourfold as much dansyl fluorescence as that of 5% PS (FIG. 6D).

Figures 6E, 6F:
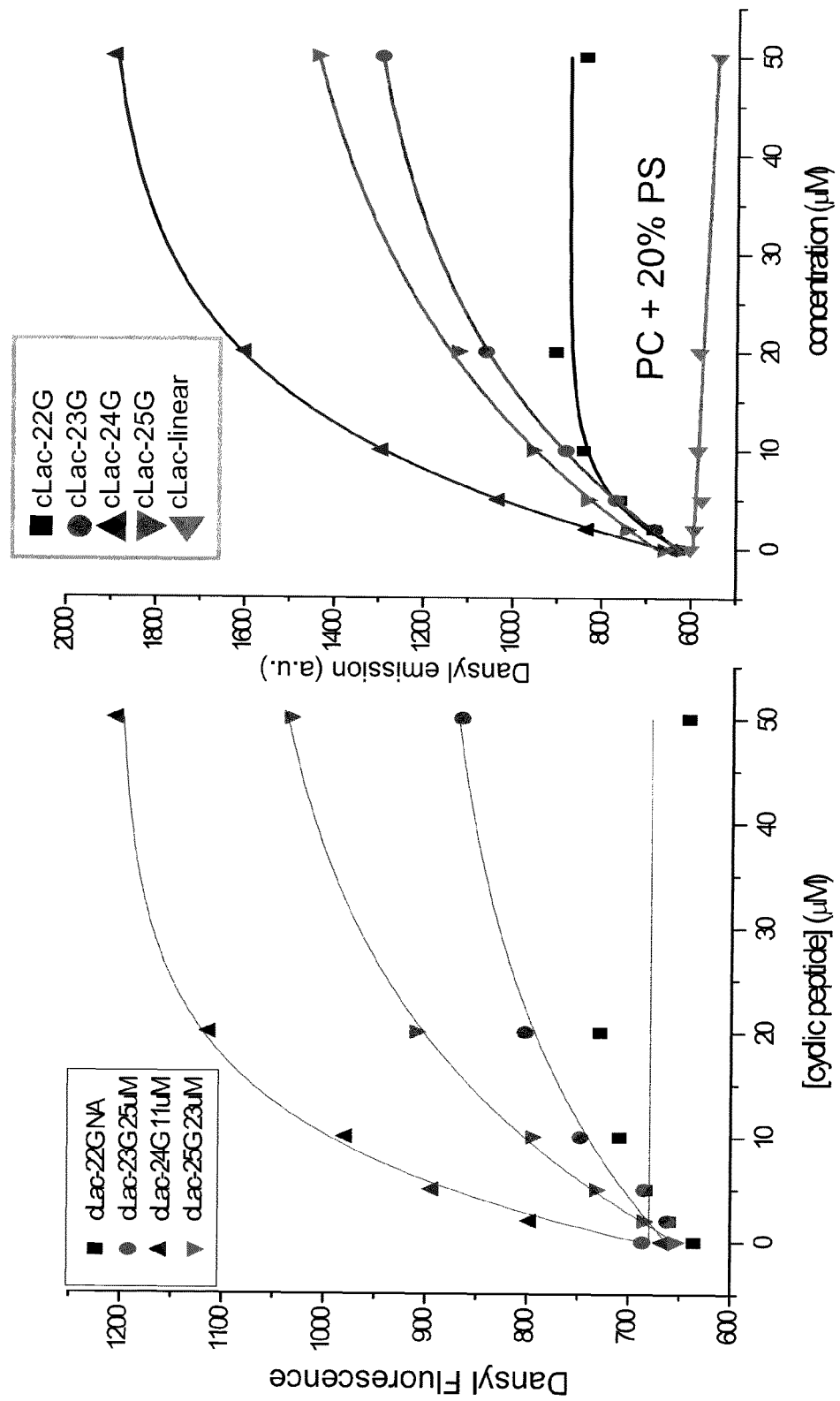
FIG. 6E shows a SAR (structure activity relationship) study of cLac-2 to compare cLac peptide variants having different linker lengths.
FIG. 6F shows a SAR (structure activity relationship) study of cLac to compare the linear precursor and cLac-2 peptide variants having different linker lengths.
Figure 7:
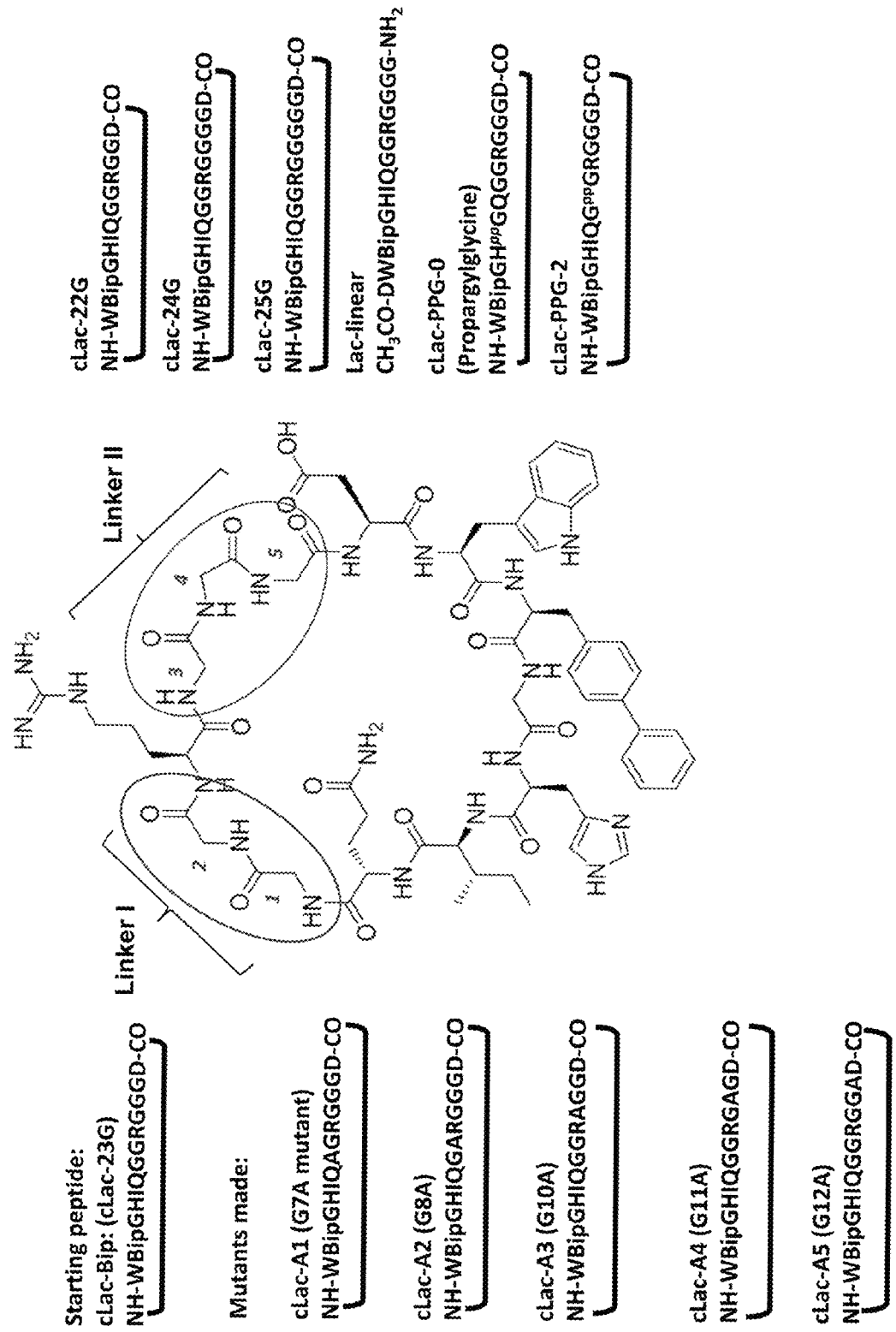
FIG. 7 depicts exemplary alanine substituted for glycine linker cLac peptide variants made.
Figure 8:
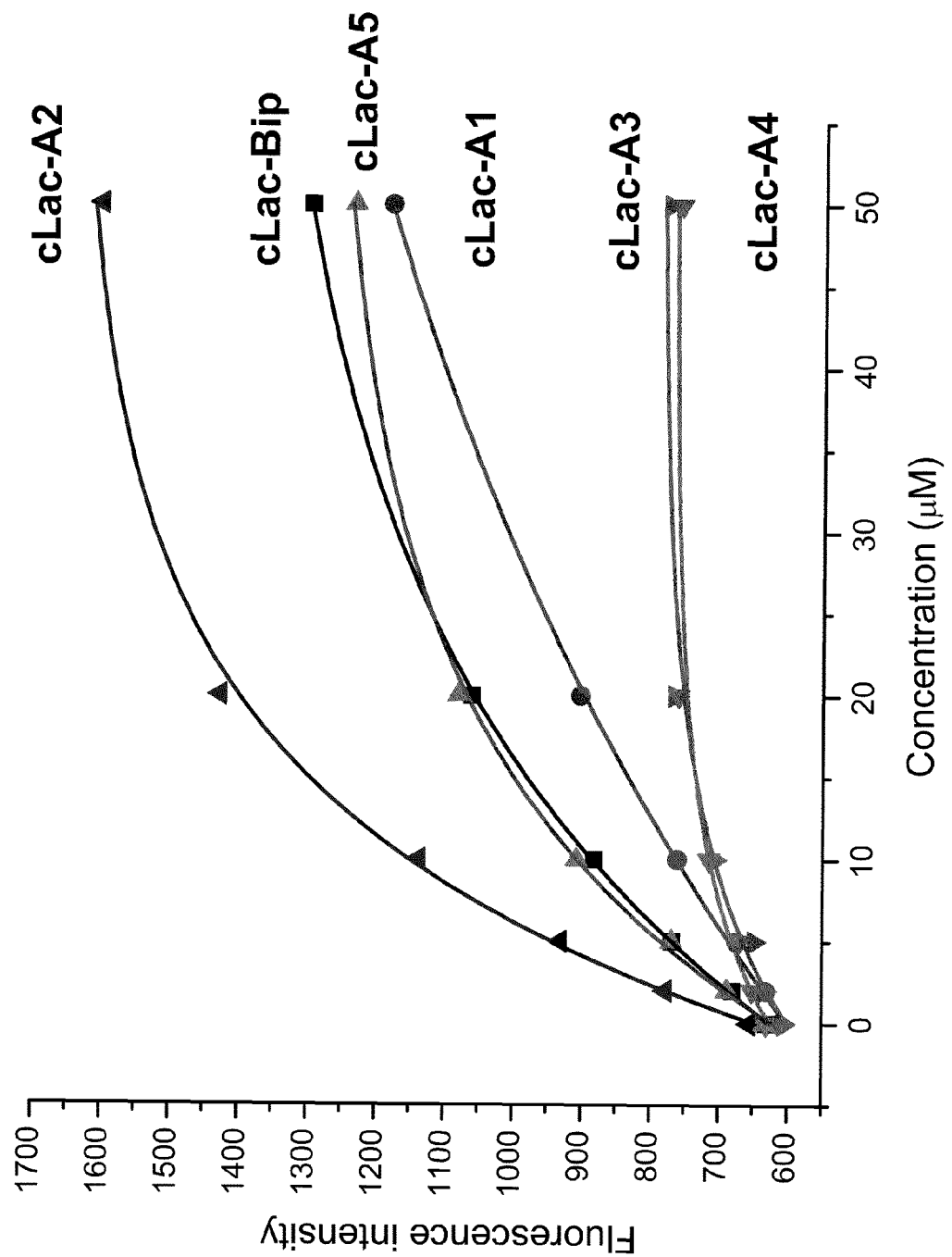
FIG. 8 depicts a SAR study showing the binding of alanine substituted for glycine linker cLac peptide variants to 20% PS (compared to cLac-Bip, the parent cLac peptide), indicating that geometries and distances of functional groups are important for PS binding affinity.

Further study of the structure-activity relationship showed that the linear precursor of cLac-2 binds to neither type of vesicle (FIG. 6F), indicating that the circular arrangement of the key residues is necessary for the PS-dependent membrane association of cLac-2. The initial optimization of cLac-2 focused on the oligoglycine linkers. The number of Gly residues within linker II (as illustrated in FIG. 7) was varied from 2 to 5. The Trp-to-dansyl FRET measurements show that cLac-22G (di-Gly in linker II) elicits the lowest dansyl emission (FIGS. 6E and 6F), presumably, without wishing to be bound or limited by theory, because the linker is too short to allow the proper ring geometry for PS binding. Lengthening the linker to the tri- and tetraglycine peptides gives a continued increase in dansyl emission, indicating an improved affinity of cLac for the membrane (FIGS. 6E and 6F). Further extension to the pentaglycine linker affords a reduced dansyl emission, presumably, without wishing to be bound or limited by theory, because the excessive flexibility causes a greater entropic penalty towards membrane binding. Collectively, these data indicate that the cLac-PS binding requires the cooperative action of multiple residues and the cLac peptide successfully mimics the function of lactadherin, the protein evolved for PS recognition. Varying the length of linker I results in a less significant difference in membrane binding of the cLac variants, possibly, without wishing to be bound or limited by theory, because the perturbation of linker I can be easily attenuated by the flexible linker II (triglycine) on the other side of Arg148.

Figure 9:
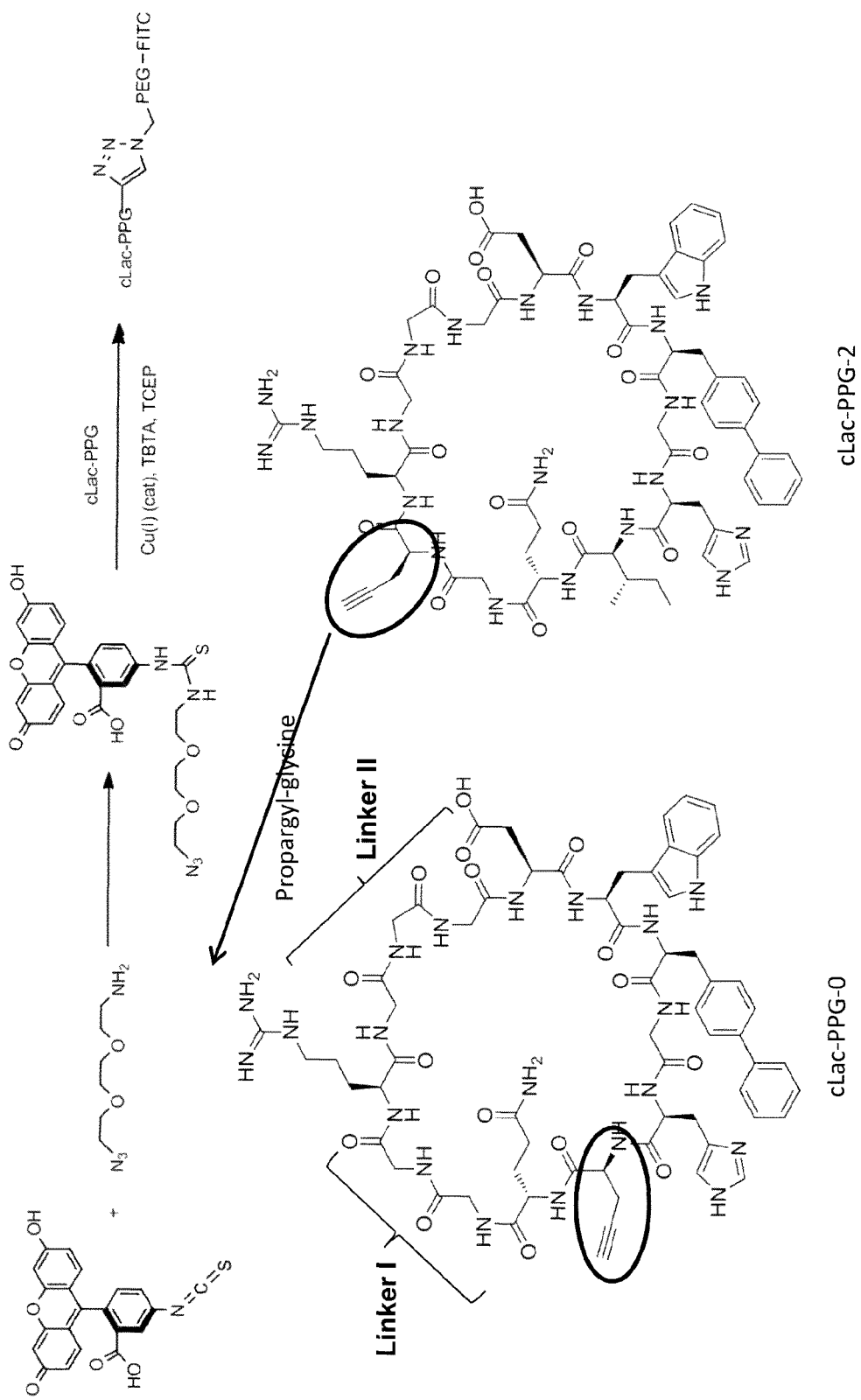
FIG. 9 shows synthesis of FITC-labeled cLac peptides using cLac-PPG peptide variants.
Figure 10B:
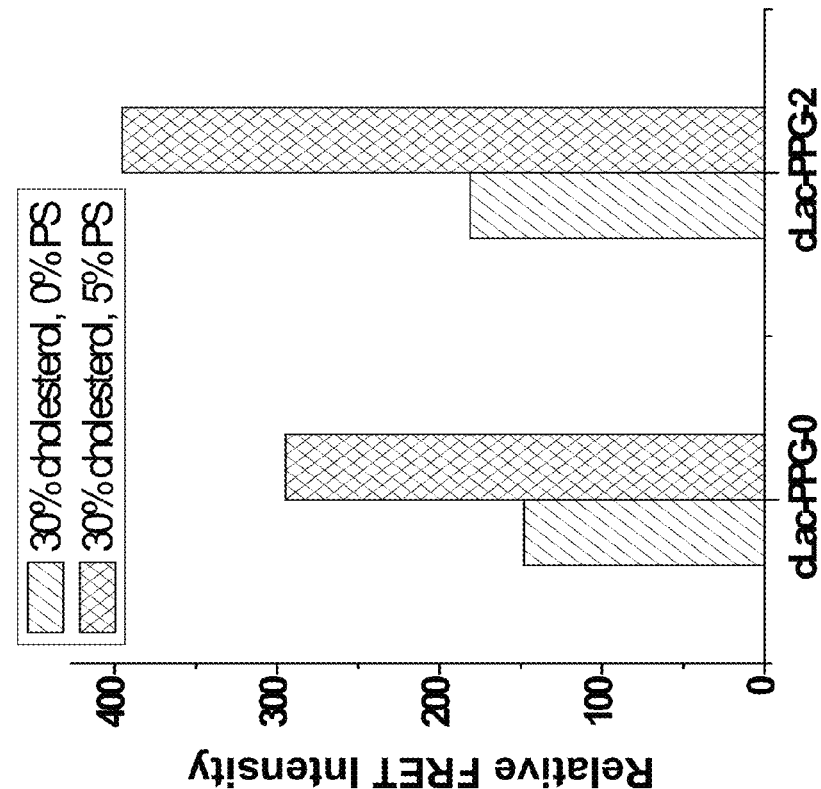
FIG. 10B shows selective binding of cLac-PPG-0 and cLac-PPG-2 to cholesterol/PS liposomes.
Figure 10A:
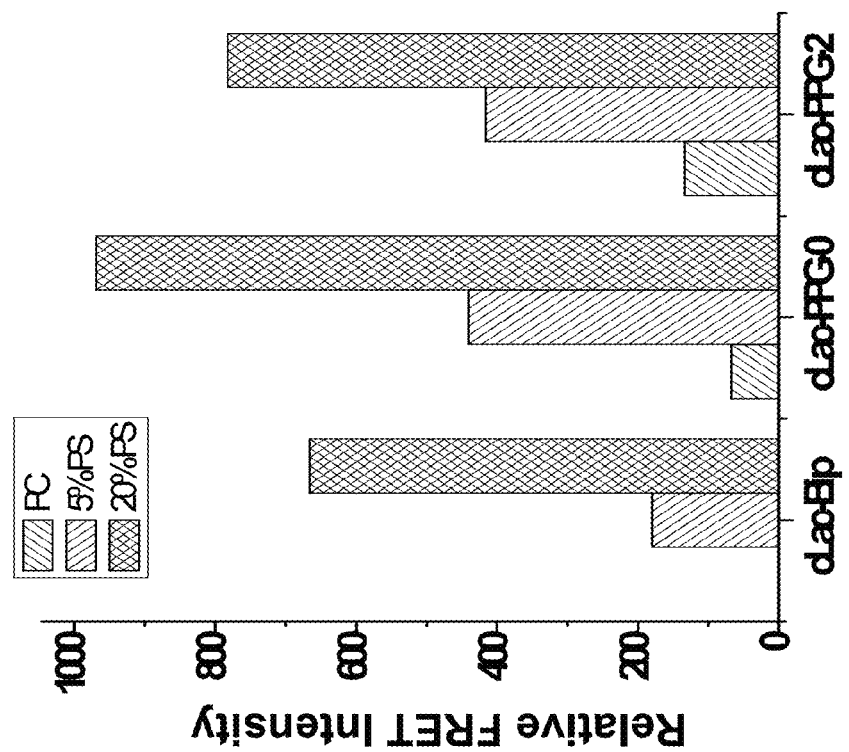
FIG. 10A shows selective binding of cLac-PPG-0 and cLac-PPG-2 to PC/PS liposomes.

In order to evaluate the potential of cLac-2 as an imaging reagent for apoptotic cells, cLac-2 was functionalized with a fluorescein label through a bioorthogonal reaction. A propargyl glycine (PPG) was introduced to replace a Gly residue within linker I (FIG. 9). This mutation site is distant from the hydrophobic and membrane inserting region of cLac; it was expected that minimal perturbation to the peptide's capability for membrane binding would occur. A fluorescein moiety was conjugated onto cLac2-PPG to give cLac2-Fl via the bioorthogonal click chemistry, in which a PEG linker bridges the fluorophore and the cyclic peptide (FIG. 9). This design introduces minimal perturbation to the specific binding of cLac and the membrane. Indeed, when the PPG derivative of cLac-2 was measured against liposomes with and without PS, membrane selectivity essentially identical to the parent peptide was observed (FIGS. 10A and 10B). The binding assay results indicate that the mutations of Ile or Gly to PPG did not change the PS selectivity of cLac peptides. The cLac peptides display PS selectivity against liposomes containing 30% cholesterol, illustrating the utility of these peptide probes in mammalian cells.

The fluorescent derivative was tested for its potential to stain apoptotic cells. Cultured HeLa and Jukat cells were treated with the potent apoptogen staurosporine (STS) or camptothecin (CPT) respectively to trigger apoptosis. The experimental conditions were optimized with the FITC-labeled annexin V and the membrane impermeable DNA intercalator propidium iodine (PI). The treatment with 0.1 μM STS or CPT for 4 hours gave a large population of early apoptotic cells (data not shown), which were stained with annexin, but not PI. This indicates increased presence of PS exposure on the outer membrane leaflet of the cells experiencing early apoptosis. Under these conditions, cLac2-Fl readily stained STS or CPT treated cells, while little fluorescence was observed for the untreated cells (data not shown). The lack of staining for the untreated cells indicated that cLac2-Fl does not get into healthy cells by diffusion or by endocytosis, as expected for most peptide-based agents, i.e., non-specific membrane interactions are absent. As negative controls, both fluorescein alone as well as the FITC-labeled linear precursor of cLac were used to label the apoptotic cells and tested for fluorescence staining. Neither control stained the apoptotic cells under the same experimental conditions, indicating cLac-Fl recognized apoptotic cells through a specific mechanism. The merged microscopic images show minimal overlay between cLac staining and the PI fluorescence (data not shown), indicating that cLac2-Fl largely detects early apoptotic cells. This observation is consistent with the previous reports that annexin V preferentially binds to cells at the early stages of apoptosis. Since these early apoptotic cells hold their membrane integrity (PI negative), it is believed cLac2-Fl stained the cells by binding to their outer surfaces, presumably to PS.

Two other human cancer cell lines (breast cancer MDA-MB-231 and colorectal cancer COLO205) will be tested to ascertain the generality of cLacs as apoptosis markers. These cells will be treated with anti-cancer drugs (e.g., staurosporine or doxorubicin) to trigger apoptosis. The treated cells, as well as the untreated controls, will be stained with the fluorescently labeled cLacs and imaged under a confocal fluorescence microscope. In addition, flow cytometry will used to quantitatively analyze the affinity and specificity of the cLac peptides towards apoptotic cells. In all these cell-based experiments, the cLac peptides will be compared to annexin V for their ability to detect apoptosis. Finally, the cytotoxicity of these cLacs will be evaluated through the commonly used MTT assay (Carmichael, J.; et al., Cancer Res 1987, 47, 936-42). The MTT assay and the MTS assay are colorimetric assays for measuring the activity of enzymes that reduce MTT or close dyes (XTT, MTS, WSTs) to formazan dyes, giving a purple color. A main application allows assessment of the viability (cell counting) and the proliferation of cells (cell culture assays). It can also be used to determine cytotoxicity of potential medicinal agents and toxic materials, since those agents would stimulate or inhibit cell viability and growth.

Improve PS Binding Affinity by Backside Stapling

The initial design of cLac incorporates two oligoglycine linkers that render the cyclic scaffold rather flexible in the unbound state. In one embodiment, the ring structure can be pre-organized to reduce the entropic penalty of binding. Pre-organization of the cLac scaffold can be achieved by making the "backside" stapled mutants (as described in FIG. 11A-11C). The backside refers to the side of cLac ring that does not form direct contact with PS in the membrane insertion side of the cLac. Introducing a covalent linkage on the backside will greatly reduce the flexibility of the cLac ring. The key to success of this approach is to ensure the backside staple does not prohibit the conformation required for PS binding.

Figures 11A, 11B, 11C, 12:
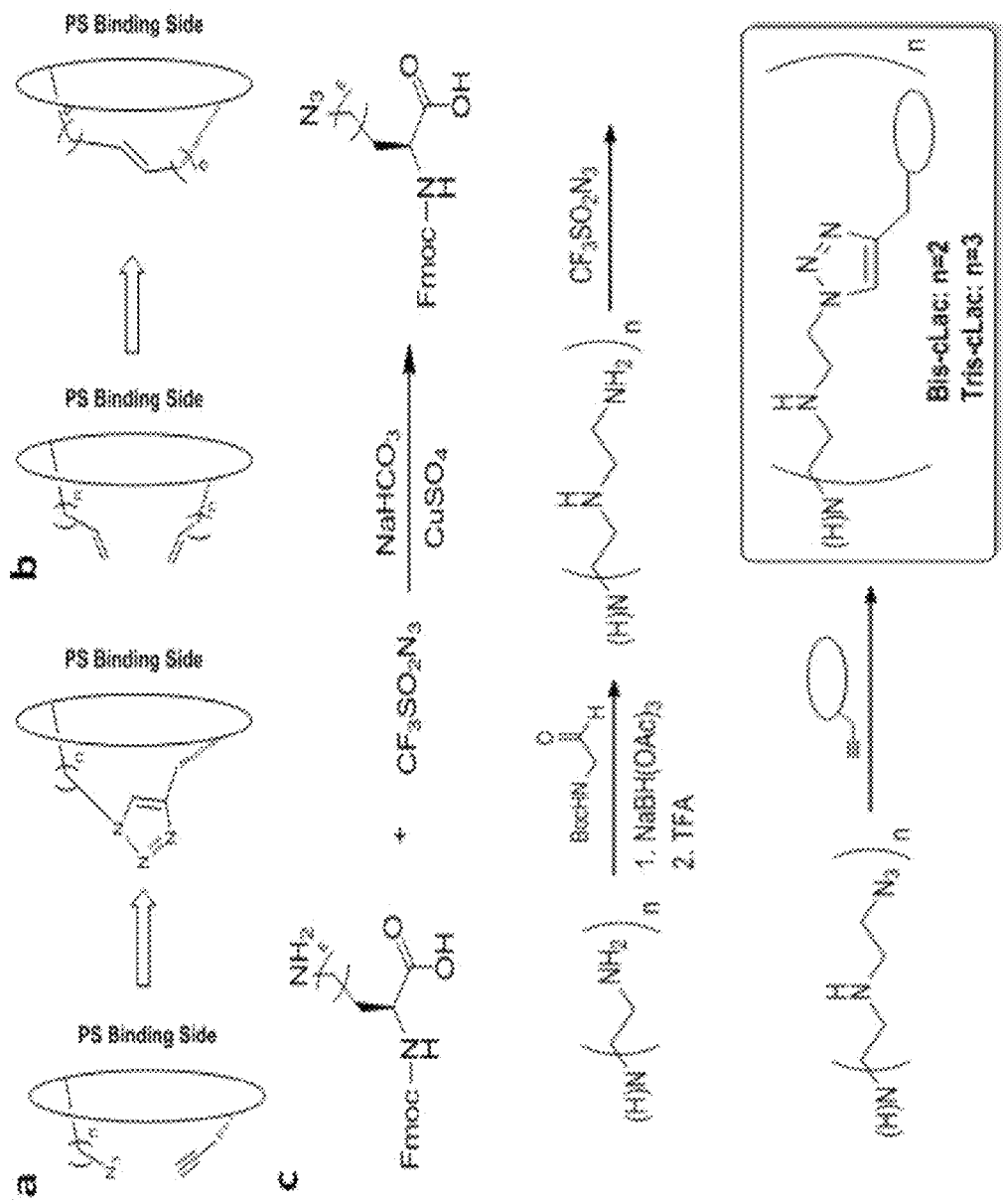
FIGS. 11A-11C show an embodiment of backside stapling to pre-organize cLac for PS binding.
FIG. 12 shows the synthetic design of the multivalent PS binding molecules. The oval shape represents the cLac ring.
Figure 14:
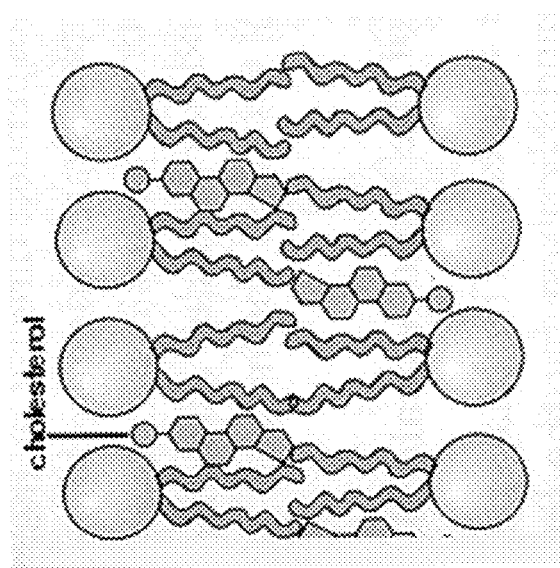
FIG. 14 shows the location of cholesterol in a typical lipid bilayer plasma membrane.

Based on the structure of Lact-C2 (FIG. 5), it is noted that the Ile side chain projects away from the PS binding side and should serve as a viable position for backside stapling. A crosslink will be introduced between the Ile residue and its diametric position, which fortuitously falls into the linker II region (FIG. 11A).

The backside staple can be introduced through either of two bioorthogonal reactions: azide-alkyne click chemistry (Best, M. D. Biochemistry 2009, 48, 6571-84) and olefin metathesis (Kim, Y. W., et al., Org Lett 2010, 12, 3046-9) (see FIGS. 11A and 11B). For the click approach, the Ile reside at position A5 of the cyclic peptide will be mutated to propargyl glycine (PPG) (See FIG. 9) and one of the Gly residues within Linker II will be replace with azido-norleucine (Anl) (see FIG. 9), which can be prepared through a one-step reaction using lysine as a starting material (Yan, R. B. et al., Tetrahedron Letters 2005, 46, 8993-8995). Anl in both the L- and D-configurations will be tested. In addition, the Anl derivatives will allow incremental variation of the length and flexibility of the backside staples. These Anl derivatives should be accessible from the corresponding derivatives of lysine (FIG. 11C). The cLac peptide variants (also known as cLac peptide mutants or cLac mutants) with azide and alkyne functionalities will be prepared through the same protocol as the cLac2 synthesis. Backside stapling can be achievable through the Cu(I)-catalyzed intramolecular click reaction. The resulting cLac mutants will be tested for PS binding through the liposome- and cell-based assays described herein. The azide-alkyne stapling strategy prevents the use of the click chemistry again to introduce fluorescent labels (see FIG. 9). This conflict will be resolved by utilizing thiol- or amine-reactive fluorophores for labeling shown in FIG. 13

The backside stapling can also be introduced through olefin metathesis (FIG. 11B), for which unnatural amino acids with terminal alkenes are introduced into cLac at the same positions described above (FIG. 11B). Ru-catalyzed intramolecular olefin metathesis will readily yield the backside crosslinked cLac. The advantage of this approach lies in the commercial availability of the series of unnatural, alkene-derivatized amino acids with varying stereochemistry and side chain length. The hydrophobic olefin crosslink and the hydrophilic triazoles can also be used.

Improve PS Binding Affinity by Multivalency

The PS binding affinity of cLac can be improved by the multivalent effect. The oligomers of cLac2 will be prepared again through the bioorthogonal click chemistry, for which the unnatural amino acid PPG will be used for conjugation. Since the linker I region will be reserved for fluorophore labeling, PPG will be introduced into linker II, which is also remote from the membrane inserting motif of cLac2. It has been shown that PPG replacing a Gly in linker I does not perturb the PS binding potential. The same is expected for mutations in the linker II region. The azido-derivatized polyamine scaffolds will be used to prepare the cLac dimers and trimers (FIG. 12): bis and tris-(2-aminoethyl)amine will be extended by reductive amination with the aldehyde derivative of Boc-Gly followed by removal of the BOC protecting group. The reason for this extension is to avoid overcrowding within the cLac oligomers that may compromise PS binding. The terminal amines will be converted into azides using TfN3, the same chemistry utilized to make azido-norleucine as shown in FIG. 11. (Yan, R. B., et al., Tetrahedron Letters 2005, 46, 8993-8995). Conjugation of the polyazides with the alkyne-decorated cLac will yield the dimeric and trimeric constructs using Cu(I) catalysis. The cLac oligomers will be tested for PS binding through the Trp-to-dansyl FRET assay. Furthermore, thiol or amine functionalities will be incorporated into linker I for conjugation with fluorescent labels. The labeled oligo-cLacs will be evaluated for their potential to stain apoptotic cells. Since the oligomers carry multiple fluorophores, they may give brighter images of apoptotic cells as well.

Figure 13:
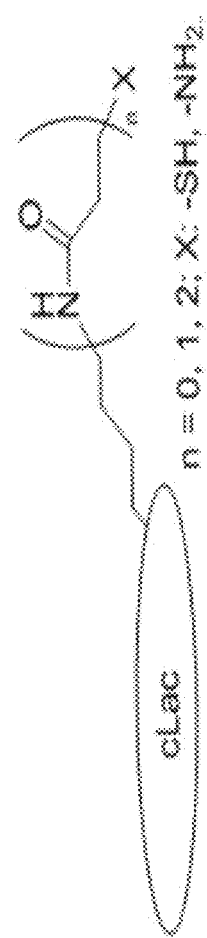
FIG. 13 shows an optimized design of cLac for labeling with commercially available dyes.
Figure 15B:
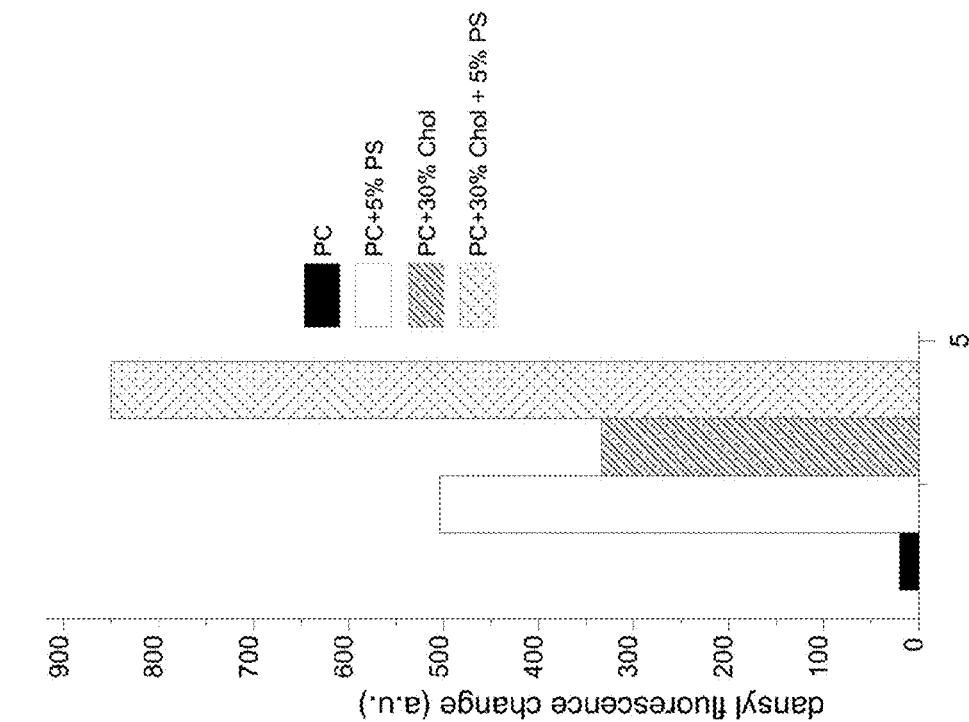
FIG. 15B are histograms showing the effect of cholesterol on specific PS binding activity of cLac-2 with PC and PC/PS liposomes.
Figure 15A:
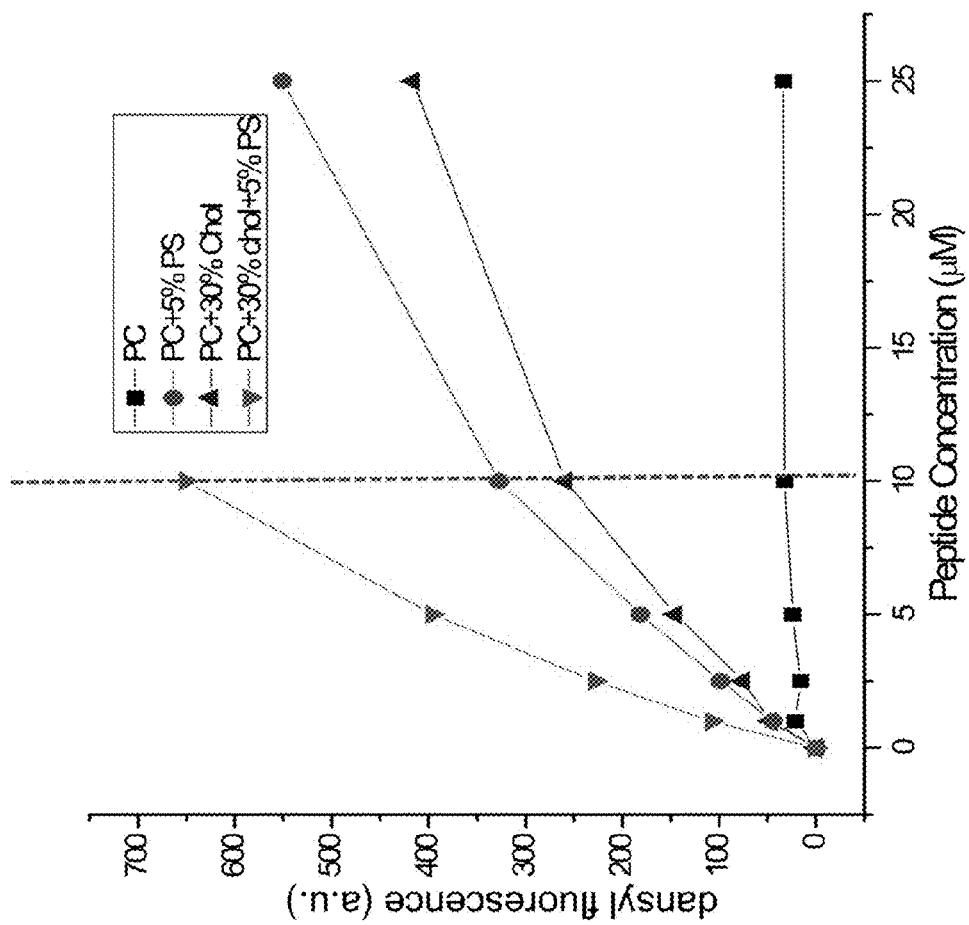
FIG. 15A shows graphically the effect of cholesterol on specific PS binding activity of cLac-2 to PC and PC/PS liposomes.

Commercially available dyes are largely reactive to thiols and amines. It increases the scope of applications for cLac by being labeled with commercially available dyes, particularly the near infra-red ones used for in vivo imaging. Cys and Lys respectively will be incorporated to replace PPG within cLac2-PPG (FIG. 11). The Cys mutant will be labeled with fluorescein-5-maleimide (5-MF) and the Lys variant will be labeled with 5/6-carboxyfluorescein succinimidyl ester (5/6-FAM SE). Since cLac2 does not have other nucleophilic residues except the one introduced for labeling, the fluorophore conjugation should be a rather clean reaction. The cLac-Flcan can also be made to extend the linker length by using a trityl-protected Lys. After peptide cyclization on resin, the trityl group will be removed and the Lys side chain will be extended with one or two β-alanines. The amino group of β-alanine is expected to react with 5/6-FAM SE readily to yield the fluorescently labeled cLac peptide (FIG. 13). Instead of β-alanine, the use of β-mercaptopropionic acid as the last monomer will give a terminal thiol group for labeling.

cLac Peptide Variants with Aromatic Anchor Region for Selective Membrane Recognition at the Hydrophobic Motif Comprising A1 and A2 Residues The original cyclic cLac peptide, cLac-Bip, displayed non-specific binding to cholesterol-containing membranes of liposomes (FIG. 15). While not wishing to be held in theory, cholesterol may induce cLac binding into PC vesicles presumably due to negative curvature. Nevertheless, even with the presence of cholesterol, cLac-Bip was able to differentiate PS-containing vesicles from PS-absent vesicles (FIG. 15).

Figure 17:
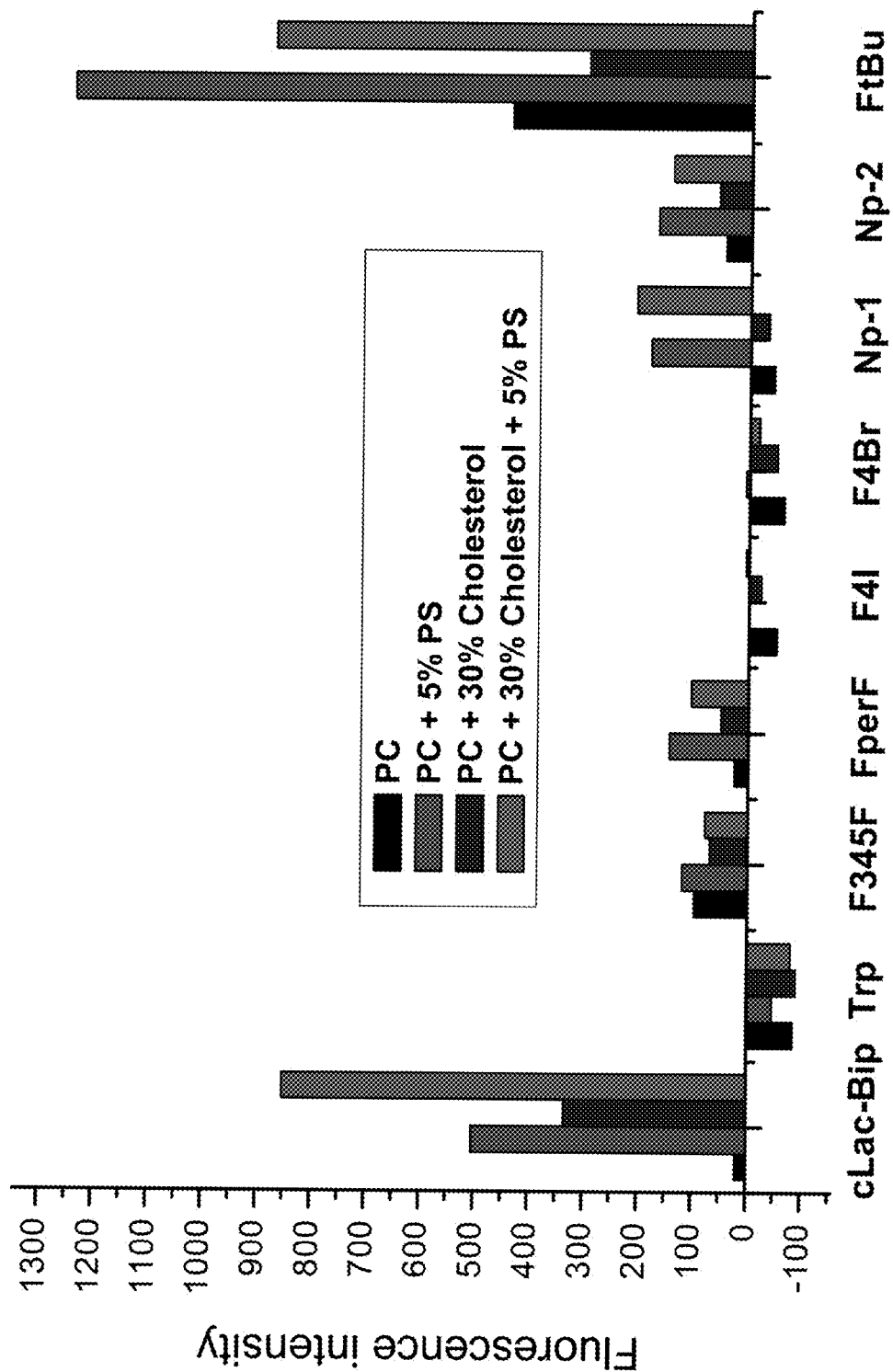
FIG. 17 are histograms showing the specific PS binding activity of cLac peptide variants having unnatural amino acids at the A2 hydrophobic residue position.

FIG. 17 shows that cholesterol influence can be minimized by optimizing the aromatic residues (hydrophobic) that serve as membrane anchors in the A1 and A2 positions of the cyclic peptide. Several cLac peptide variants were made using the unnatural amino acids having the various aromatic side chains shown in FIG. 16. The data shows a variety of unnatural amino acids are able to give PS-selective membrane insertion. While all variants give PS sensitivity, the cLac-naphthalene (cLac-Np-1) variant displays essentially no binding to cholesterol containing membranes, while it binds readily into vesicles with PS (see FIG. 17). Therefore, we expect cLac-Np-1 to serve as a better PS imaging probe.

The references cited herein and throughout the specification are incorporated herein by reference.

Table 1 Showing Hydropathy Index of the Twenty Common Naturally Occurring Amino Acids

| Amino Acid | 3- Letter | 1- Letter | Side chain polarity | Side chain charge (pH 7) | Hydropathy index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | neutral | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

Examples of cLac variant peptides and activities

| Peptide Name | SEQ. ID. NO. | Peptide sequence | Liposome binding assay | Cell imaging |
|---|---|---|---|---|
| Lac-1: | 35 | WGHIQGRGGGD | N | N/A |
| Lac-1R: | 36 | GGGRGQIHGWD | N | N/A |
| Lac-2: | 37 | WGHIQGGRGGGD | N | N/A |
| Lac-Phe; cLac-1 | 38 | WFGHIQGGRGGGD | N | N/A |
| Lac-Bip; cLac-Bip; cLac-2; or cLac-23G | 1 | WBipGHIQGGRGGGD | Y | N/A |
| Lac-Tph: | 39 | WTphGHIQGGRGGGD | Nonselective | N/A |
| cLac-A1 (G7A mutant): | 2 | WBipGHIQAGRGGGD | Y | N/A |
| cLac-A2 (G8A) | 3 | WBipGHIQGARGGGD | Y | N/A |
| cLac-A3 (G10A) | 40 | WBipGHIQGGRAGGD | N | N/A |
| cLac-A4 (G11A) | 41 | WBipGHIQGGRGAGD | N | N/A |
| cLac-A5 (G12A) | 4 | WBipGHIQGGRGGAD | Y | N/A |
| cLac-13G | 9 | WBipGHIQGRGGGD | Y | N/A |
| cLac-33G | 10 | WBipGHIQGGGRGGGD | Y | N/A |
| cLac-22G | 42 | WBipGHIQGGRGGD | N | N/A |
| cLac-24G | 5 | WBipGHIQGGRGGGGD | Y | N/A |
| cLac-25G | 6 | WBipGHIQGGRGGGGGD | Y | N/A |
| cLac-PPG-0 | 7 | WBipGH$^{pp}$GQGGRGGGD | Y | Y |
| cLac-PPG-2 | 11 | WBipGHIQG$^{pp}$GRGGAD | Y | Y |
| cLac-D-Trp | 12 | DWBipGHIQGGRGGGD | Y | N/A |
| cLac-linear | 43 | DWBipGHIQGGRGGG | N | N |

"Y" means PS-selective (or apoptotic cell-specific) binding is observed,
N means no or insignificant membrane binding is observed,
N/A means that the experiment was not carried out.
"Nonselective" refers to membrane binding independent on PS.
DW = D-Tryptophan.
ppG = propargyl glycine.
Liposome binding assay is the dansyl FRET assay.
Cell imaging is by standard epifluorescence micposcopy known in the art.

We claim:

1. A cyclic peptide comprising at least 11 but no more than 20 amino acid residues having the formula I:

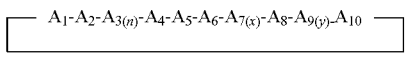

wherein $A_1$ is either tryptophan or d-tryptophan;
wherein $A_2$ is biphenylalanine ("Bip");
wherein $A_4$ is an amino acid with polar side chain that can form strong hydrogen bonding or salt bridge, the hydrogen bonding or salt bridge having a bond strength from 10 to >155 kJ mol$^{-1}$;
wherein $A_5$ is a small hydrophobic amino acid selected from the group consisting of isoleucine, alanine, valine, leucine and methionine;
wherein $A_6$ is an amino acid with polar side chain that can form strong hydrogen bonding, the hydrogen bonding having a bond strength from 10 to >155 kJ mol$^{-1}$;
wherein $A_3$, $A_7$ and $A_9$ are neutral amino acid residues, wherein n=1-3, x=1-5 and y=2-6, and when there are multiples of $A_3$, $A_7$ and $A_9$, they can be the same amino acid residues or different amino acid residues;
wherein $A_8$ is a positively charged amino acid; and
wherein $A_{10}$ is an amino acid with a negatively charged side chain.

2. The cyclic peptide of claim 1, wherein $A_4$ is selected from the group consisting of histidine, asparagine, glutamine, lysine, arginine and the respective analogues and derivatives thereof.

3. The cyclic peptide of claim 1, wherein $A_6$ is selected from the group consisting of glutamine, tyrosine, serine, asparagine, histidine, cysteine and threonine.

4. The cyclic peptide of claim 1, wherein $A_3$, $A_7$ and $A_9$ are each individually selected from the group consisting of glycine, alanine, valine, leucine, isoleucine, cysteine, tyrosine, tryptophan, serine, threonine, proline, methionine, phenylalanine, glutamine, asparagine and propargyl glycine (ppG).

5. The cyclic peptide of claim 1, wherein $A_3$, $A_7$ and $A_9$ are each individually alanine or glycine.

6. The cyclic peptide of claim 1, wherein $A_8$ is selected from the group consisting of lysine, arginine and the analogues and derivatives of these amino acids.

7. The cyclic peptide of claim 1, wherein $A_{10}$ is selected from the group consisting of aspartic acid, glutamic acid and the analogues and derivatives of these amino acids.

8. The cyclic peptide of claim 1, wherein the cyclic peptide binds to phosphatidylserine.

9. The cyclic peptide of claim 1, wherein the cyclic peptide is selected from the group consisting of WBipGHIQG-GRGGGD (SEQ ID NO: 1), WBipGHIQAGRGGGD (SEQ ID NO: 2), WBipGHIQGARGGGD (SEQ ID NO: 3), cLac-A5 or WBipGHIQGGRGGAD (SEQ ID NO: 4), WBipGHIQGGRGGGD (SEQ ID NO: 5), WBipGHIQG-GRGGGGD (SEQ ID NO: 6), WBipGHppGQGGRGGGD (SEQ ID NO: 7), WBipGHIQGppGRGGGD (SEQ ID NO: 8), WBipGHIQGRGGGD (SEQ ID NO: 9), WBipGHIQGGGRGGGD (SEQ ID NO: 10), WBipGHIQGpppGRGGAD (SEQ ID NO: 11), d-WBipGHIQGGRGGGD (SEQ ID NO: 12) or a peptide variant thereof.

10. The cyclic peptide of claim 1, further comprising a label.

11. A composition comprising a cyclic peptide of claim 1 and a pharmaceutically acceptable carrier.

12. A kit comprising a cyclic peptide of claim 1 and instructions for using the cyclic peptide or composition to detect phosphatidylserine exposure or apoptosis in a sample.

13. A method of detecting phosphatidylserine exposure on a cell, comprising contacting a biological sample with the cyclic peptide of claim 1 and measuring the cyclic peptide attached to the biological sample, wherein the amount of cyclic peptide attached is above a reference level indicates the presence of phosphatidylserine exposure on a cell in the biological sample.

14. A method of detecting apoptosis of a cell, comprising contacting a biological sample with the cyclic peptide of claim 1 and measuring the cyclic peptide attached to the biological sample, wherein the amount of cyclic peptide attached is above a reference level indicates the presence of apoptosis in the biological sample.

15. A method of detecting apoptosis in a tissue in a subject in need thereof, contacting the tissue with the cyclic peptide of claim 1 and measuring the cyclic peptide attached to the tissue, wherein the amount of cyclic peptide attached is above a reference level indicates the presence of apoptosis in the tissue.

16. A kit comprising a composition of claim 11 and instructions for using the cyclic peptide or composition to detect phosphatidylserine exposure or apoptosis in a sample.

17. A method of detecting phosphatidylserine exposure on a cell, comprising contacting a biological sample with a composition of claim 11 and measuring the cyclic peptide attached to the biological sample, wherein the amount of cyclic peptide attached is above a reference level indicates the presence of phosphatidylserine exposure on a cell in the biological sample.

18. A method of detecting apoptosis of a cell, comprising contacting a biological sample with a composition of claim 11 and measuring the cyclic peptide attached to the biological sample, wherein the amount of cyclic peptide attached is above a reference level indicates the presence of apoptosis in the biological sample.

19. A method of detecting apoptosis in a tissue in a subject in need thereof, contacting the tissue with or a composition of claim 11 and measuring the cyclic peptide attached to the tissue, wherein the amount of cyclic peptide attached is above a reference level indicates the presence of apoptosis in the tissue.

\* \* \* \* \*